(12) United States Patent
Awasthi et al.

(10) Patent No.: US 9,173,839 B2
(45) Date of Patent: Nov. 3, 2015

(54) ANIONIC LIPIDS AND LIPID NANO-STRUCTURES AND METHODS OF PRODUCING AND USING SAME

(71) Applicants: Vibhudutta Awasthi, Edmond, OK (US); Pallavi Lagisetty, Glen Allen Richmond, VA (US)

(72) Inventors: Vibhudutta Awasthi, Edmond, OK (US); Pallavi Lagisetty, Glen Allen Richmond, VA (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 387 days.

(21) Appl. No.: 13/863,000

(22) Filed: Apr. 15, 2013

(65) Prior Publication Data

US 2013/0243688 A1 Sep. 19, 2013

Related U.S. Application Data

(62) Division of application No. 12/556,906, filed on Sep. 10, 2009, now Pat. No. 8,420,118.

(51) Int. Cl.
| | |
|---|---|
| *A61K 9/127* | (2006.01) |
| *A61K 31/02* | (2006.01) |
| *A61K 9/00* | (2006.01) |
| *B01J 13/02* | (2006.01) |
| *A61K 38/00* | (2006.01) |

(52) U.S. Cl.
CPC .............. *A61K 9/127* (2013.01); *A61K 9/0026* (2013.01); *A61K 9/1272* (2013.01); *A61K 9/1277* (2013.01); *B01J 13/02* (2013.01); *A61K 38/00* (2013.01)

(58) Field of Classification Search
CPC ...................................................... A61K 9/127
USPC ..................................... 424/450; 264/4.1, 4.3
See application file for complete search history.

(56) References Cited

U.S. PATENT DOCUMENTS

| | | | |
|---|---|---|---|
| 5,296,231 | A | 3/1994 | Yarosh |
| 5,472,951 | A | 12/1995 | Saitoh et al. |
| 6,864,094 | B2 | 3/2005 | Tsuchida et al. |
| 6,949,663 | B2 | 9/2005 | Tsuchida et al. |
| 6,965,049 | B2 | 11/2005 | Tsuchida et al. |
| 7,417,118 | B2 | 8/2008 | Kai et al. |
| 2004/0258745 | A1 | 12/2004 | Kai et al. |
| 2006/0110438 | A1 | 5/2006 | Suematsu et al. |

FOREIGN PATENT DOCUMENTS

| | | |
|---|---|---|
| DE | 4238032 | 10/1994 |
| WO | 2005-063212 | 7/2005 |
| WO | 2005-079185 | 9/2005 |

OTHER PUBLICATIONS

Keitaro Sou, et al; "Effective Encapsulation of Proteins into Size-Controlled Phospholipid Vesicles Using Freeze—Thawing and Extrusion"; Biotechnol. Prog. 19; 2003; p. 1547-1552.
Vibhudutta Awasthi; "Pharmaceutical Aspects of Hemoglobin-Based Oxygen Carriers"; Current Drug Delivery, 2; 2005; p. 133-142.

(Continued)

*Primary Examiner* — Gollamudi Kishore
(74) *Attorney, Agent, or Firm* — Dunlap Codding, P.C.

(57) ABSTRACT

Anionic non-phospholipids, as well as lipid nanostructures formed therefrom, are disclosed herein. Also disclosed are methods of producing and using same.

8 Claims, 13 Drawing Sheets

(56) References Cited

OTHER PUBLICATIONS

Hideki Abe et al.; "Interaction of Hemoglobin Vesicles, a Cellular-Type Artificial Oxygen Carrier, with Human Plasma: Effects on Coagulation, Kallikrein-Kinin, and Complement Systems"; Artificial Cells, Blood Substitutes, and Biotechnology, 34: 1-10; 2006.

Vibhudutta Awasthi, et al.; "Insertion of poly (ethylene glycol)-lipd reduces the lipsome-encapsulated hemoglobin-induced thrombocytopenic reaction"; American Journal of Pharmacology and Toxicology 2 (2): 98-105; 2007.

Hideki Abe et al.; "Effects of Hemoglobin Vesicles, a Liposomal Artificial Oxygen Carrier, on Hematological Responses, Complement and Anaphylactic Reactions in Rats"; Artificial Cells, Blood Substitute, and Biotechnology, 35: 157-172; 2007.

Keitaro Sou, et al.; "Electrostatic interactions and complement activation on the surface of phospholipid vesicle containing acidic lipids: Effect of the structure of acidic groups"; Biochimica et Biophysica Acta 1778; 2008; p. 1035-1041.

Awasthi, V.D., et al.; "Neutral and Anionic liposome-encapsulated hemoglobin: Effect of postinserted poly(ethylene glycol)-distearoylphosphatidylethanolamine on distribution and circulation kinetics"; J. Pharmacol. Exp. Ther., vol. 309: 241-248 (2004).

Baseline scan → Hemorrhage → Post-hemorrhage scan → Resuscitation → Post-resuscitation scan

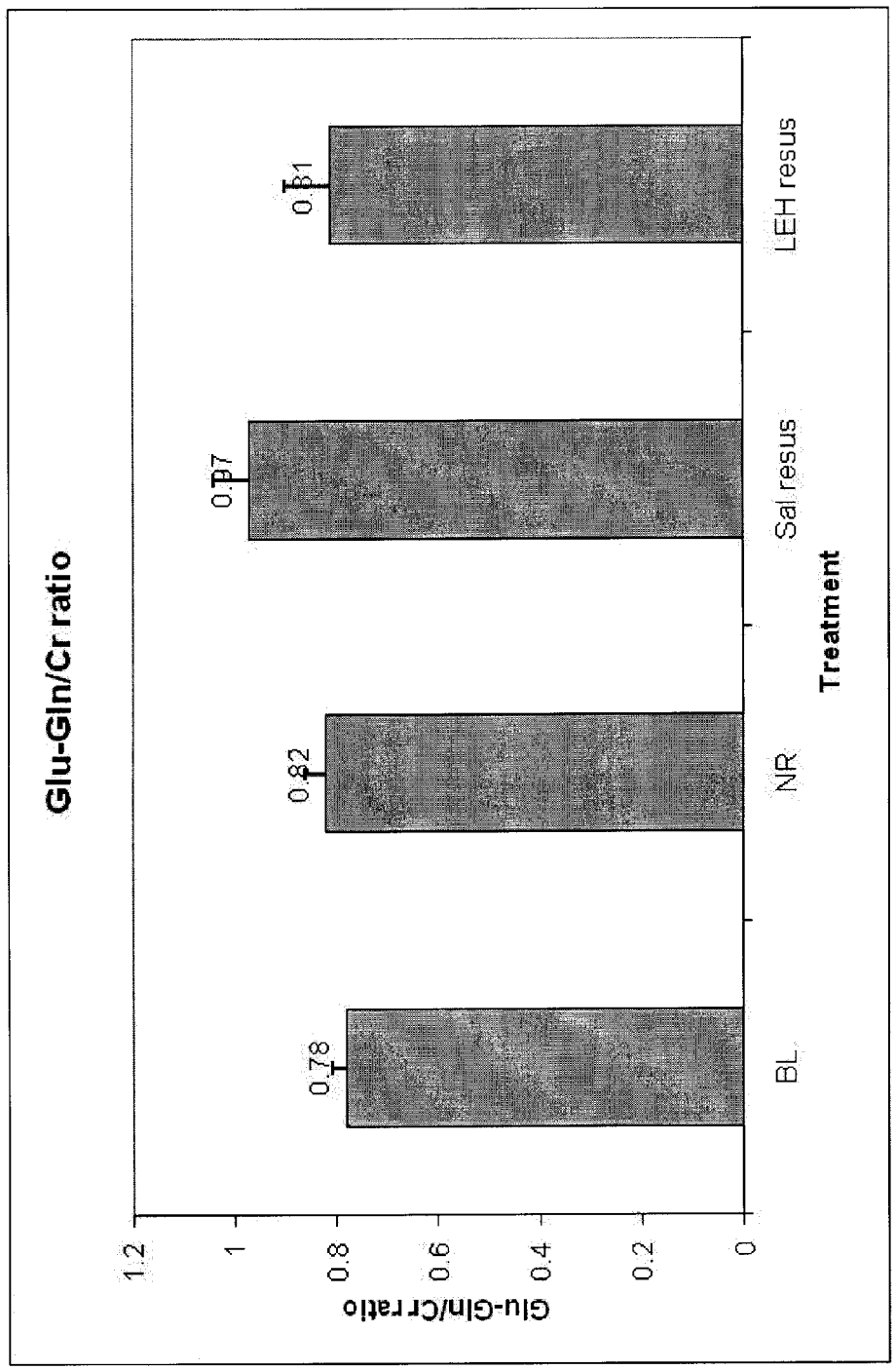
Figure 11 – Con't.
Baseline scan → Hemorrhage → Post-hemorrhage scan → Resuscitation → Post-resuscitation scan

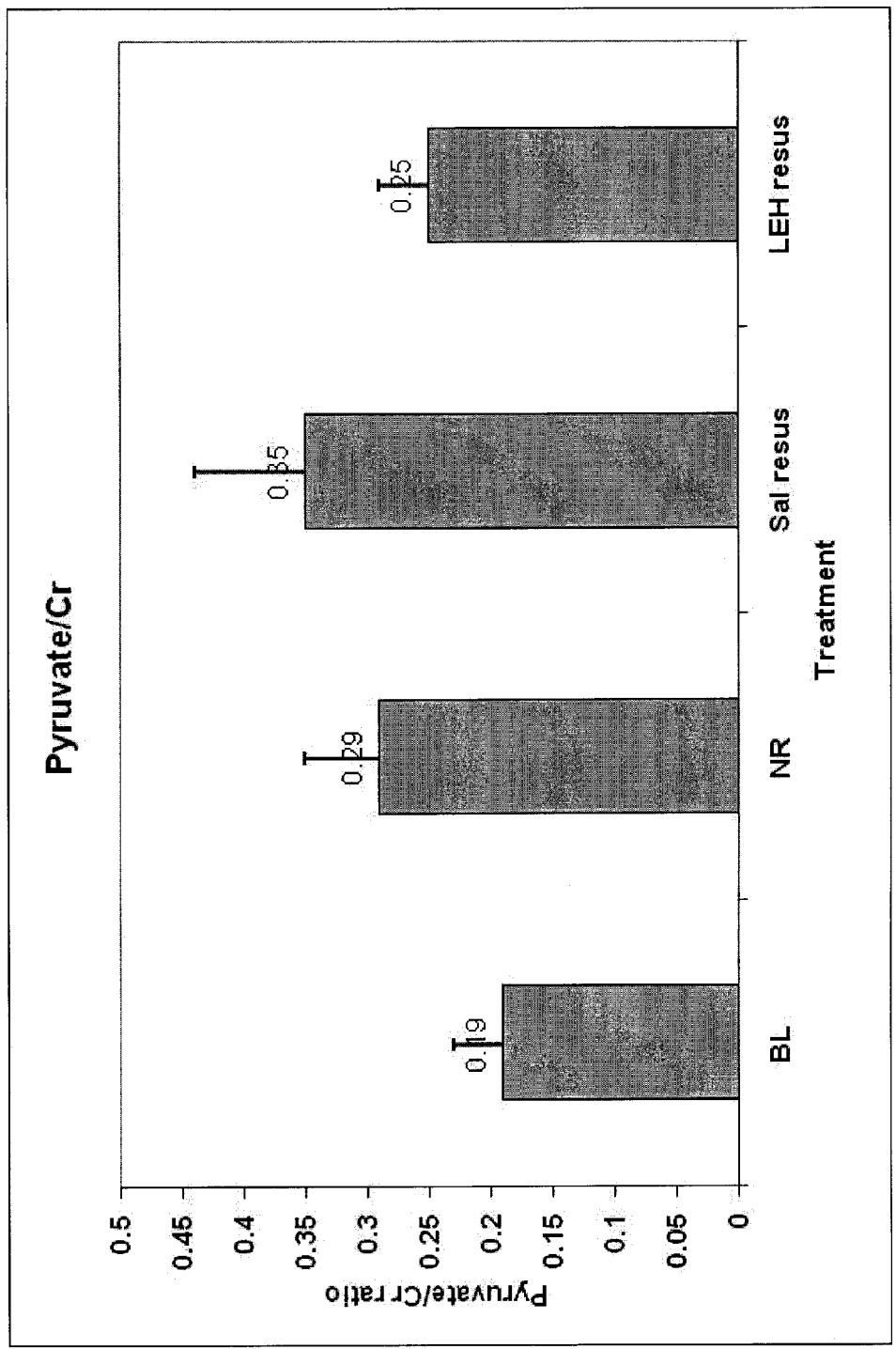
Figure 11 – Con't.
Baseline scan → Hemorrhage → Post-hemorrhage scan → Resuscitation → Post-resuscitation scan

Figure 11 – Con't.
Baseline scan → Hemorrhage → Post-hemorrhage scan → Resuscitation → Post-resuscitation scan
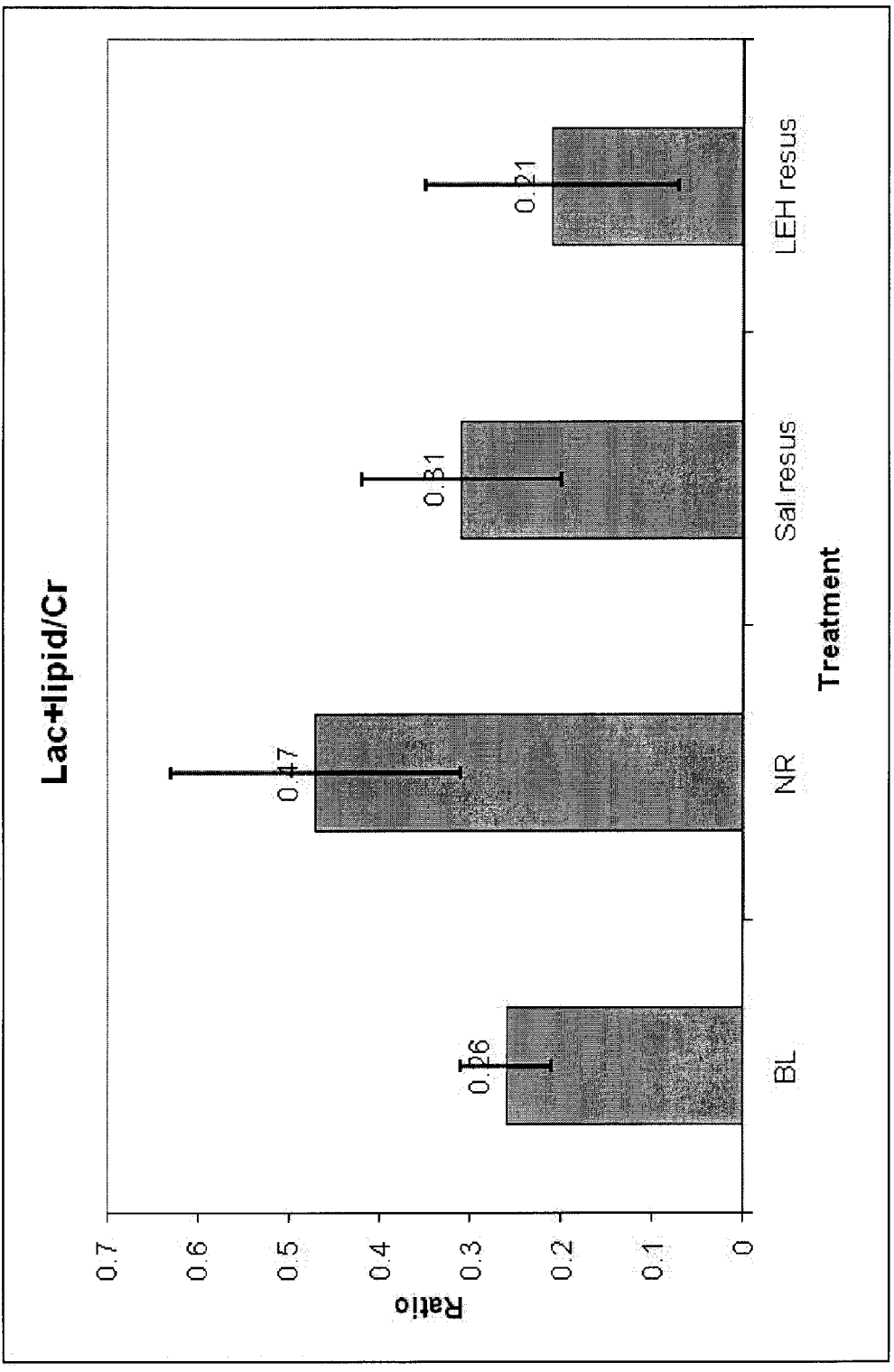

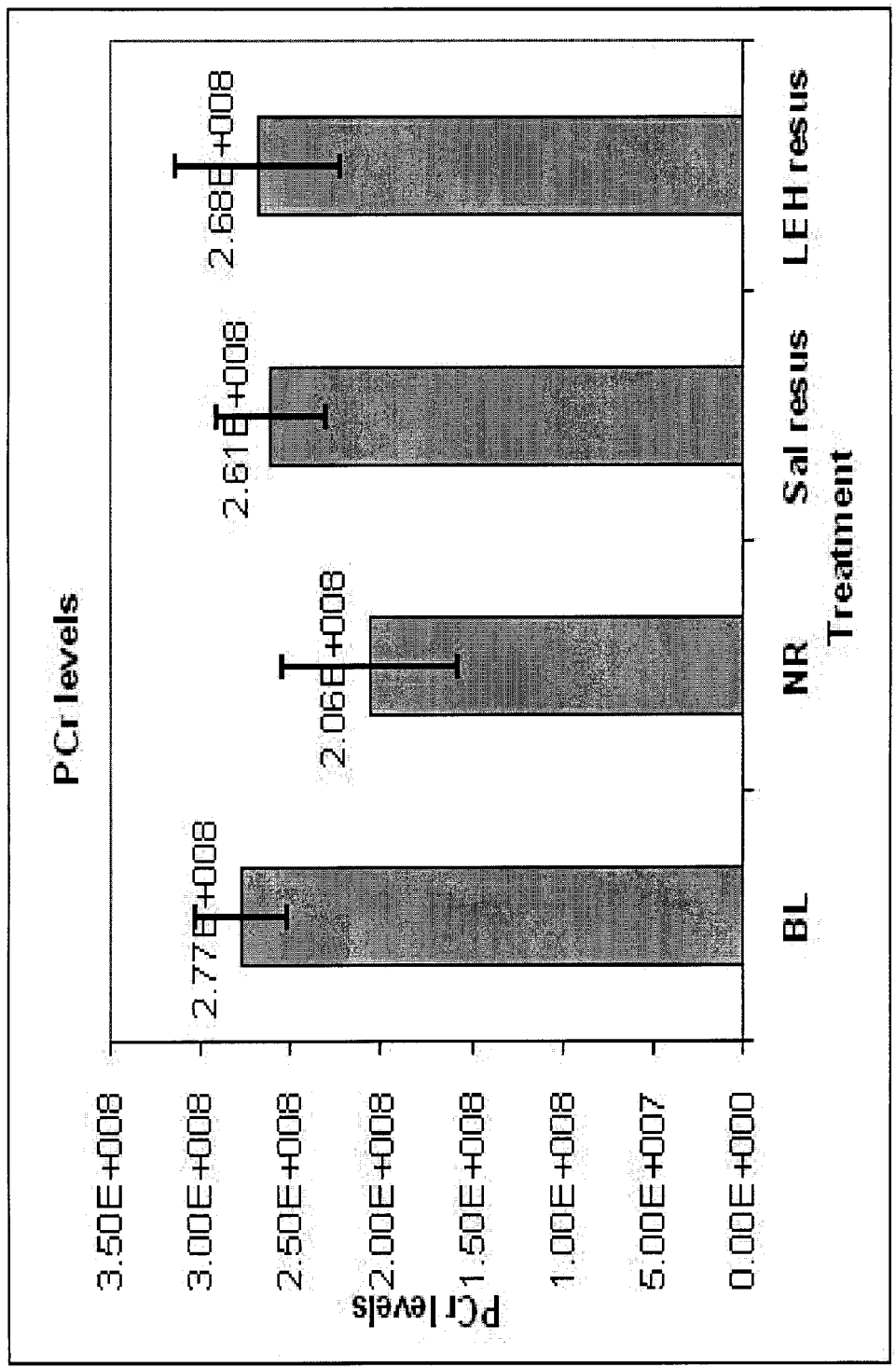
Figure 11 – Con't.
Baseline scan → Hemorrhage → Post-hemorrhage scan → Resuscitation → Post-resuscitation scan

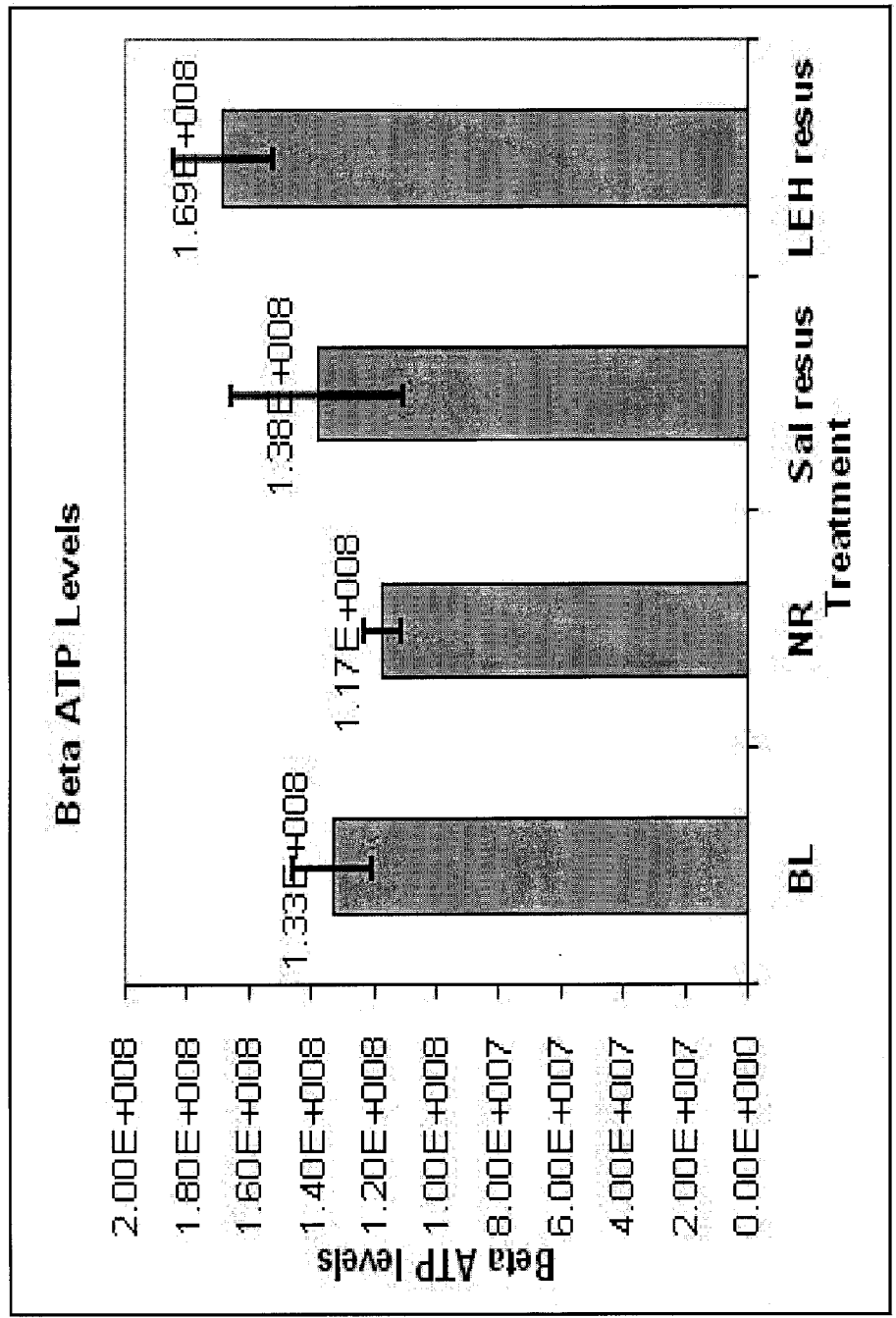
Figure 11 – Con't.
Baseline scan → Hemorrhage → Post-hemorrhage scan → Resuscitation → Post-resuscitation scan

ANIONIC LIPIDS AND LIPID NANO-STRUCTURES AND METHODS OF PRODUCING AND USING SAME

CROSS REFERENCE TO RELATED APPLICATIONS/INCORPORATION BY REFERENCE STATEMENT

This application is a divisional of U.S. Ser. No. 12/556,906, filed Sep. 10, 2009. The entire contents of the above-referenced patent application are expressly incorporated herein by reference.

STATEMENT REGARDING FEDERALLY SPONSORED RESEARCH OR DEVELOPMENT

This inventive concept(s) was made with government support under Contract Number EB005187 awarded by the National Institutes of Health. The government has certain rights in the inventive concept(s).

BACKGROUND

1. Field of the Inventive Concept(s)

The presently disclosed and claimed inventive concept(s) relates generally to compositions comprising encapsulation materials, and in particular, but not by way of limitation, to compositions comprising anionic lipids without a phosphate group, and methods of producing and using same.

2. Description of the Background Art

Vesicles encapsulating useful substances in the internal aqueous phase and their dispersions are an important technology in various fields such as pharmaceuticals, perfumes, cosmetics and food stuffs. Examples of widely used lipids that constitute the membrane of the vesicle/liposome include negatively charged (anionic) phospholipids. Anionic phospholipids have previously been used in liposomes for imparting size-stability, enhancing encapsulation of pharmaceuticals and/or to modulate pharmacokinetics and pharmacodynamics of liposomes. However, said anionic phospholipids have been shown to induce untoward reactions in biological systems, and the resultant toxicity has been manifested by severe side effects such as but not limited to, acute thrombocytopenia, complement activation, dysfunction of white blood cells and the like.

Safety and adequate availability of blood is still a major concern in transfusion medicine. The requirement of pre-transfusion processing, storage and cross-matching of blood are other factors that have given impetus to the search for safe, shelf-stable and efficacious oxygen carrying fluids. An oxygen carrying fluid mimicking red blood cells (RBCs), in efficacy and safety profile is the goal. An ideal oxygen carrier would be hemoglobin that is encapsulated and is supplemented with the oxido-reductive system of RBC. One approach to compartmentalize hemoglobin is to encapsulate hemoglobin in liposomes [Awasthi, 2005; Phillips et al., 1999; Takaori et al., 1996; Usuba et al., 1994; Sakai et al., 1993; Farmer et al., 1988]. This encapsulated product has been variably termed hemoglobin vesicles (HbV), neo-red cells (NRC) or liposome-encapsulated hemoglobin (LEH), and said product contains highly concentrated (>36 g/dl) purified hemoglobin within the phospholipid membranes. Hemoglobin vesicles or liposome-encapsulated hemoglobin (LEH) mimics membrane enclosed cellular structure of red blood cells [Phillips et al., 1999; Sakai et al., 1996; Rudolph, 1995]. Compared to free modified hemoglobin preparations, LEH is characterized by spatial isolation of hemoglobin by an oxygen permeable lipid layer that eliminates the toxicity associated with free modified or unmodified hemoglobin.

A major impediment in the development of LEH has been the low encapsulation efficiency of hemoglobin inside the vesicles. To increase the encapsulation of proteins inside liposomes, anionic lipids, such as dimyristoyl- and dipalmitoyl-phosphatidyl glycerol (DMPG and DPPG) are usually incorporated in the lipid composition [Drummond et al., 1999; Walde et al., 2001]. However, anionic liposomes rapidly interact with the biological system subsequent to their opsonization with complement and other circulating proteins [Miller et al., 1998; Szebeni, 1998]. Such an interaction has at least two acute consequences—a rapid uptake by the reticuloendothelial system (RES), and toxic effects, such as pseudoallergy that is manifested as vasoconstriction, pulmonary hypertension, dyspnea, drop in circulating platelets and leukocytes, etc. [Awasthi et al., 2007; Szebeni et al., 2000]. Since these reactions are mostly dependent on lipid dose, the problem is more challenging when huge quantities of liposomes need to be administered, such as in the use of LEH as a resuscitative fluid in acute blood loss. It is a challenge therefore, to encapsulate maximum amounts of hemoglobin in the least amount of lipid using anionic lipids and to keep the charge-associated toxicity in check.

Therefore, there is a need in the art for new and improved lipids and liposome encapsulation methods that increase encapsulation and stability while overcoming the untoward effects commonly seen with prior art encapsulation methods. It is to said lipid compositions and lipid nanostructures formed therefrom, as well as methods of producing and using same, that the presently disclosed and claimed inventive concept(s) is directed.

BRIEF DESCRIPTIONS OF THE DRAWINGS

Figure 5:
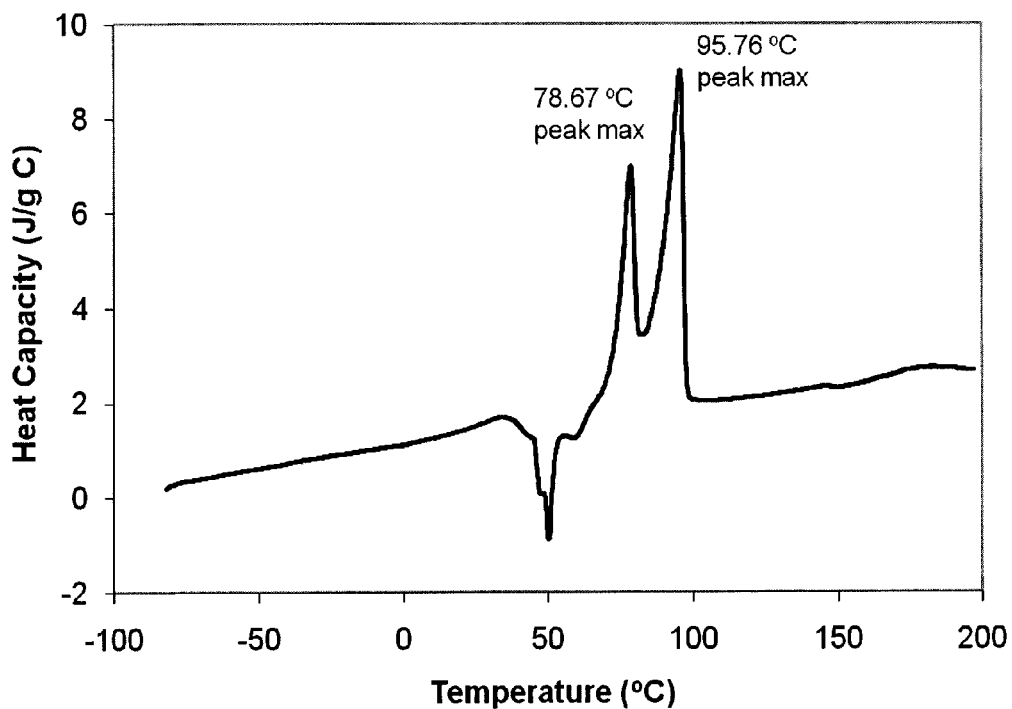

FIG. 5 graphically illustrates differential scanning calorimetry of CHHDA.

Figure 6:
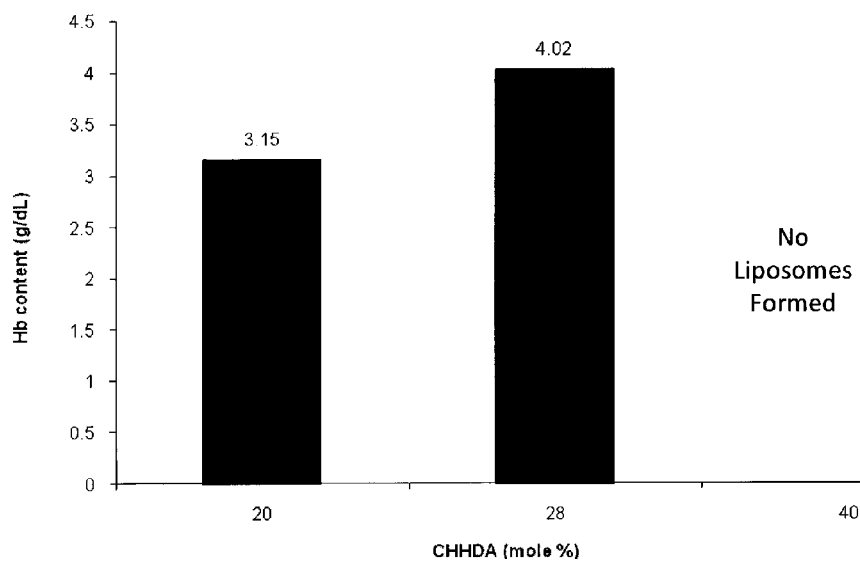

FIG. 6 illustrates the effect of CHHDA mol % on Hb encapsulation.

Figure 7:
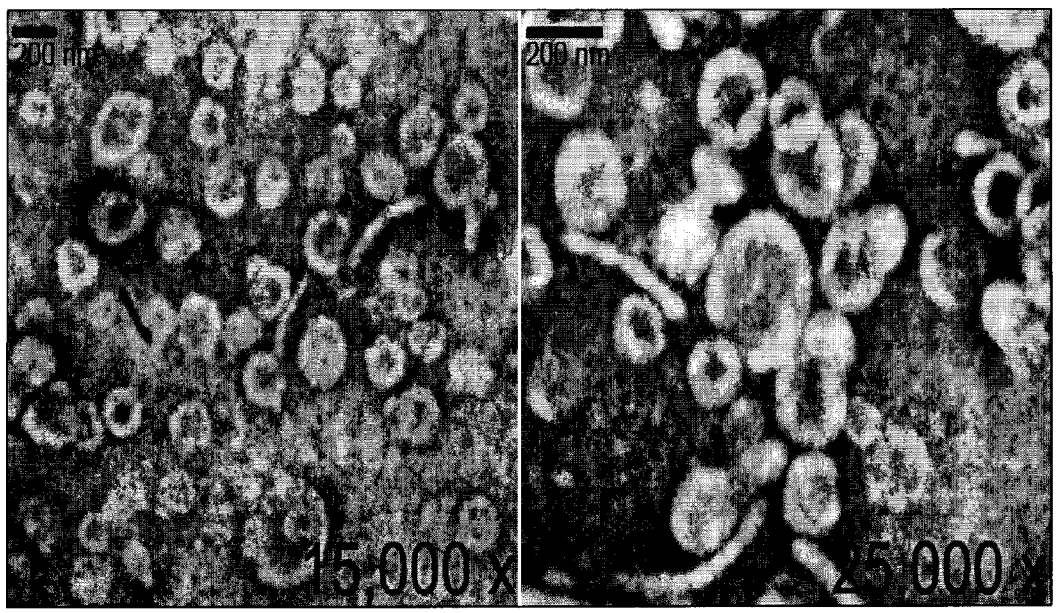

FIG. 7 contains scanning electron micrographs of LEH prepared with 28 mol % of CHHDA.

Figure 8:
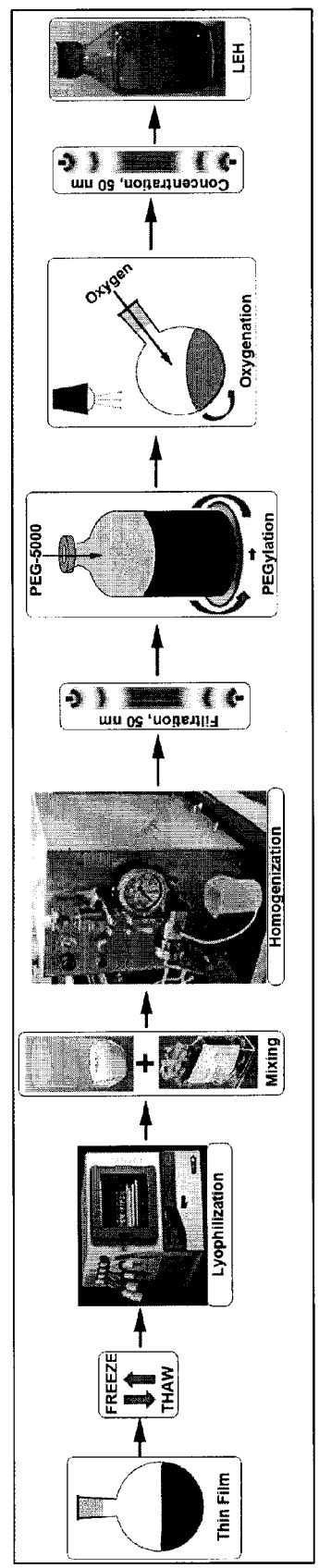

FIG. 8 is a schematic illustration of LEH manufacturing.

Figure 9A:
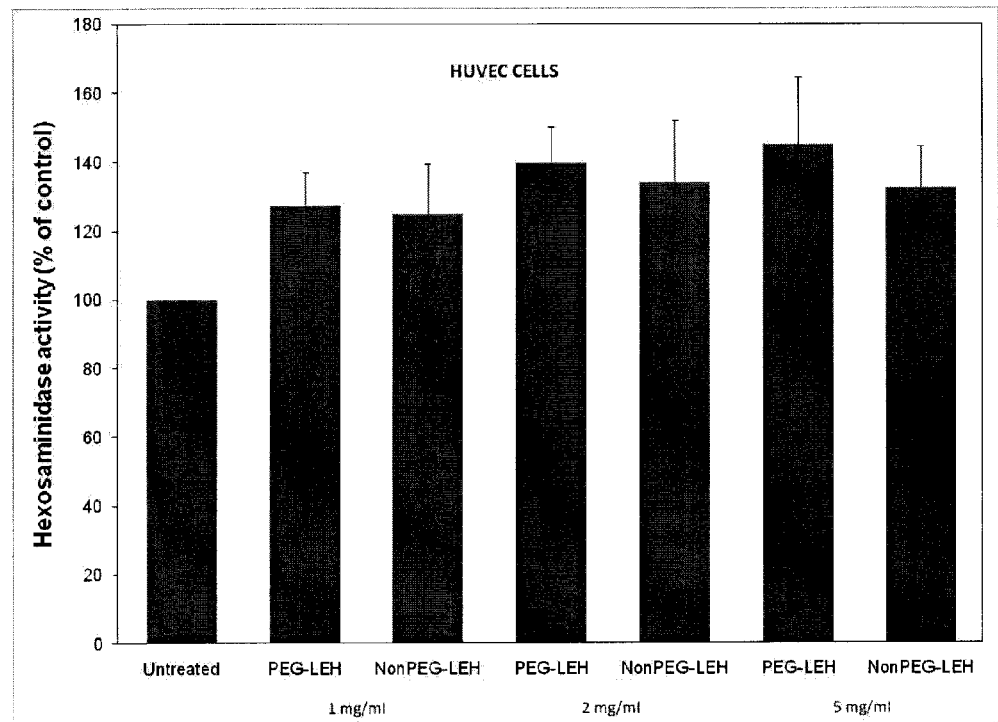
Figure 9B:
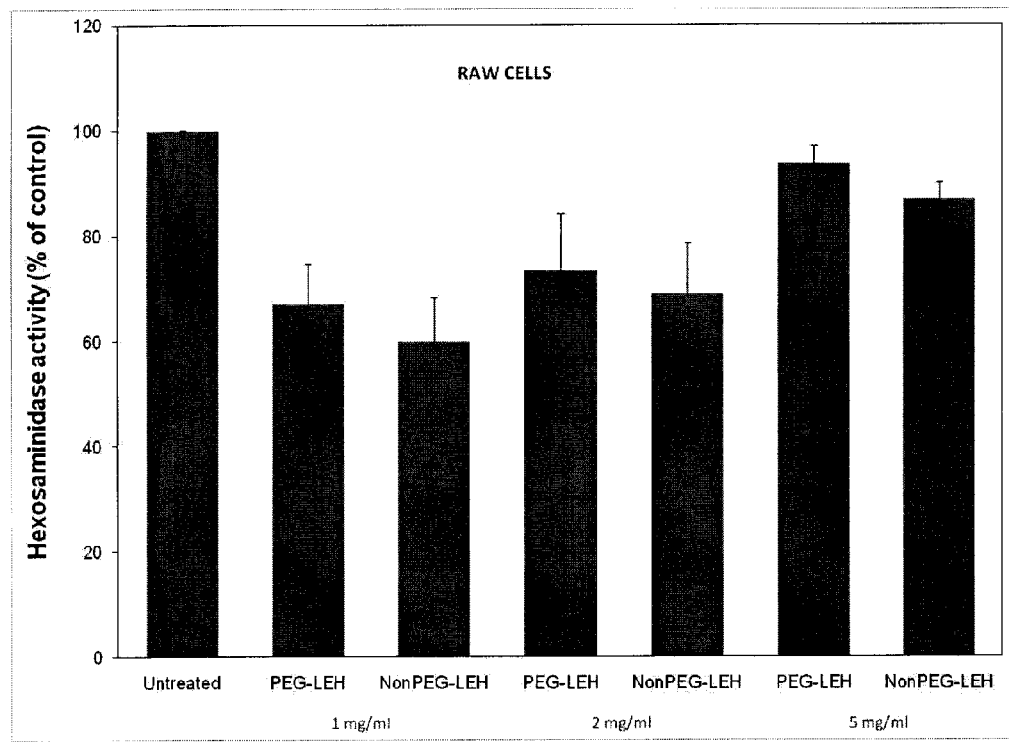

FIG. 9 graphically illustrates the cytotoxicity of LEH in HUVEC (a) and RAW cells (b).

Figure 10:
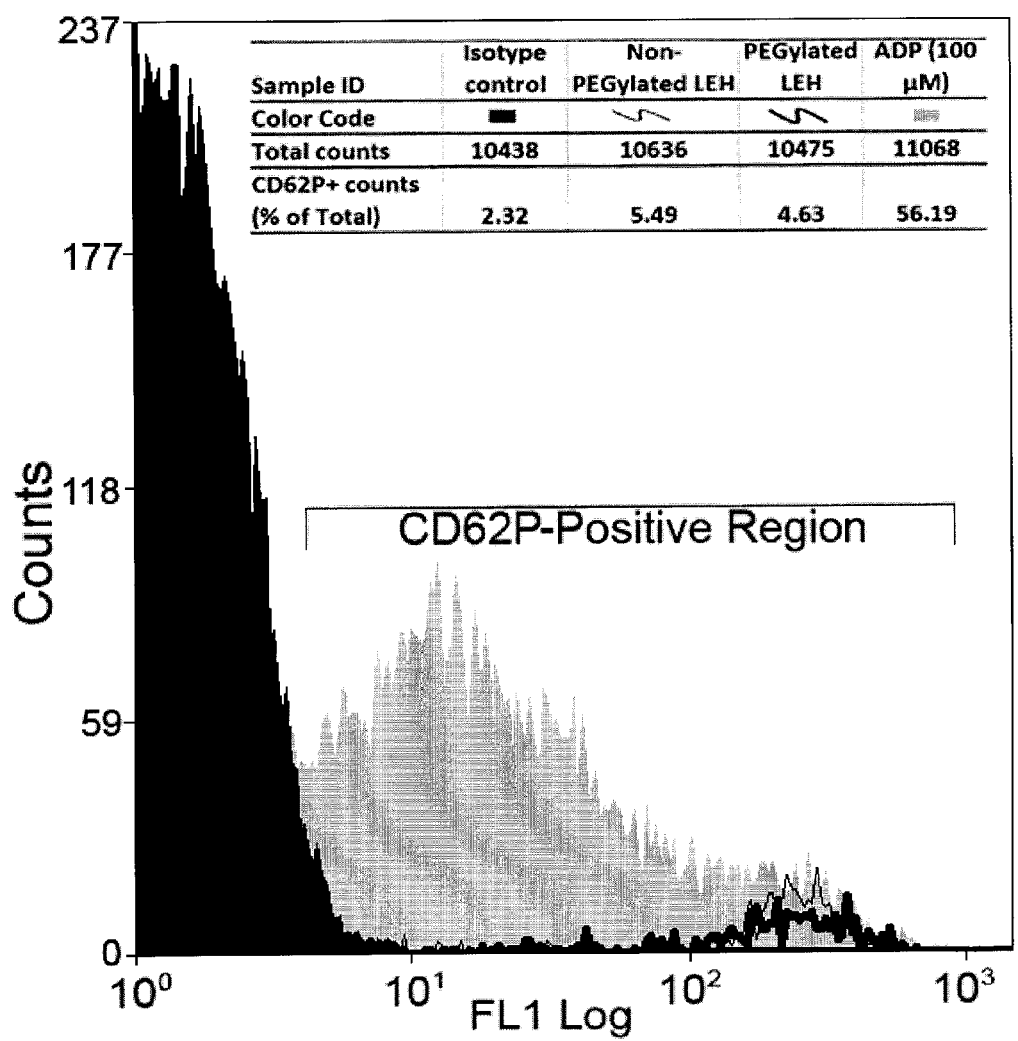

FIG. 10 demonstrates the effect of LEH on activation of platelets in vitro. ADP (100 μM) induced platelet activation, as characterized by an increase in fluorescence intensity within the CD62P-positive region. However, a similar incubation with LEH demonstrated no such platelet activation.

Figure 11:
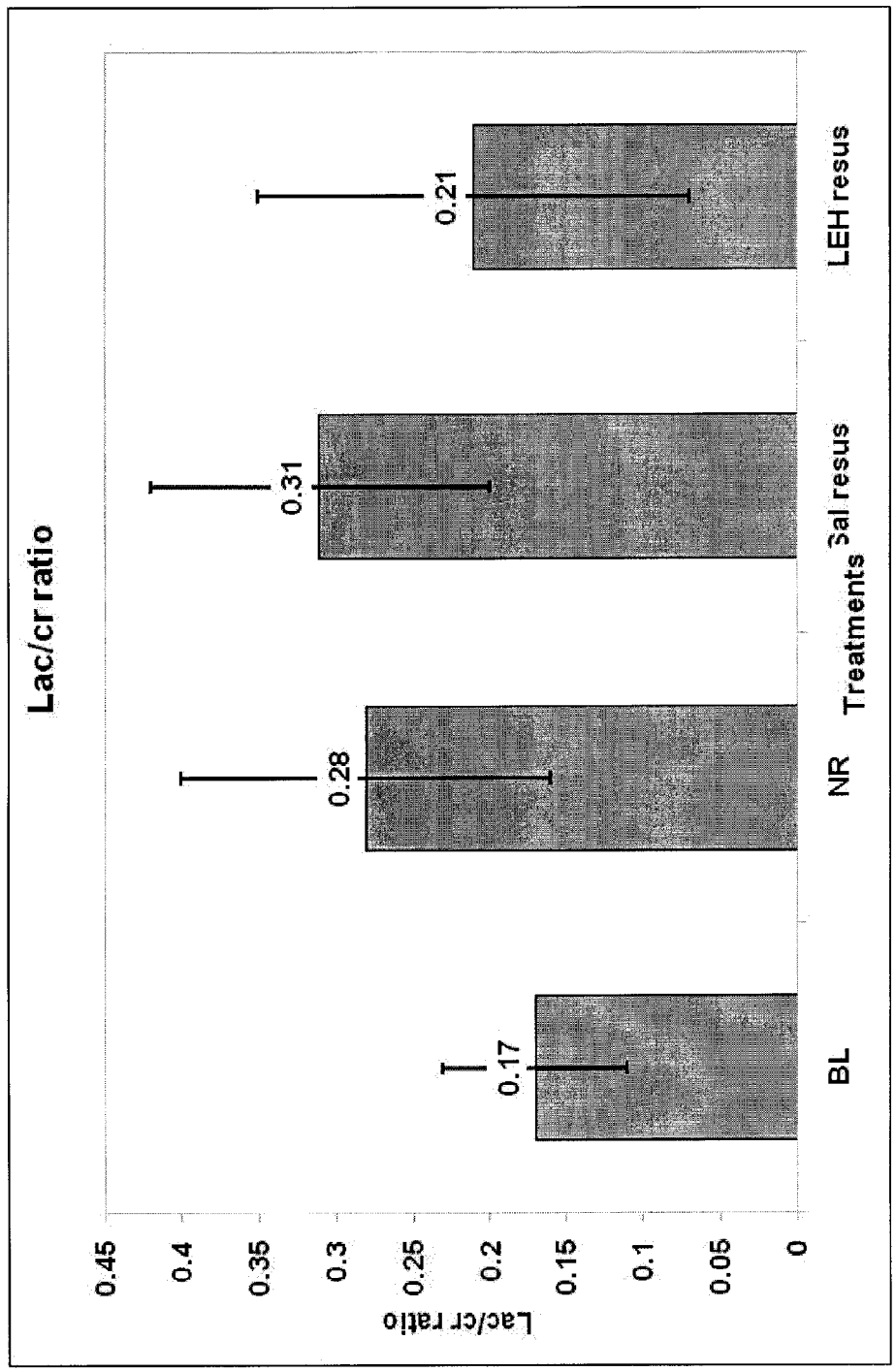

FIG. 11 graphically depicts an evaluation of effectiveness of LEH on cerebral energy metabolism in a 40% hemorrhagic shock model in rats using proton and phosphorous magnetic resonance spectroscopy ($^1$H-MRS and $^{31}$P-MRS).

DETAILED DESCRIPTION OF THE INVENTIVE CONCEPT(S)

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the inventive concept(s). The therapeutic effect may include, for example but not by way of limitation, inhibiting the growth of undesired tissue or malignant cells. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy", and will be understood to mean that the patient in need of treatment is treated or given another drug for the disease in conjunction with the pharmaceutical compositions of the presently disclosed and claimed inventive concept(s). This concurrent therapy can be sequential therapy where the patient is treated first with one drug and then the other, or the two drugs are given simultaneously.

The terms "administration" and "administering", as used herein will be understood to include all routes of administration known in the art, including but not limited to, oral, topical, transdermal, parenteral, subcutaneous, intranasal, mucosal, intramuscular and intravenous routes, including both local and systemic applications. In addition, the methods of administration may be designed to provide delayed or controlled release using formulation techniques which are well known in the art.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism. A molecule can be biologically active through its own functionalities, or may be biologically active based on its ability to activate or inhibit molecules having their own biological activity.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" as used herein includes human and veterinary subjects. "Mammal" for purposes of treatment refers to any animal classified as a mammal, including human, domestic and farm animals, nonhuman primates, and any other animal that has mammary tissue.

The terms "treat", "treating" and "treatment", as used herein, will be understood to include both inhibition of tumor growth as well as induction of tumor cell death.

Administering a therapeutically effective amount or prophylactically effective amount is intended to provide a therapeutic benefit in the treatment, prevention, or management of a disease and/or cancer. The specific amount that is therapeutically effective can be readily determined by the ordinary medical practitioner, and can vary depending on factors known in the art, such as the type of disease/cancer, the patient's history and age, the stage of disease/cancer, and the co-administration of other agents.

The terms "liposome", "lipid nanostructure" and "vesicle" may be used interchangeably herein and will be understood to refer to an assembled structure constructed of molecules such as lipids and/or proteins, for example, not through covalent bonds but through interactions (such as but not limited to, hydrophobic interactions, electrostatic interactions and hydrogen bonds) acting between the molecules in an aqueous medium.

The terms "aqueous solution" and "aqueous medium" will be used interchangeably herein and will be understood to refer to water as well as any kind of solution which is physiologically acceptable and solvent in water.

The presently disclosed and claimed inventive concept(s) is related to compositions comprising a lipid having the structure represented by the following general formula [1]:

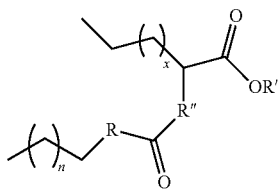

wherein R is NH or O; R' is at least one of a hydrogen (H), an alkyl group (such as but not limited to, methyl, ethyl, propyl, butyl, pentyl, hexyl, heptyl, octyl, nonyl, decyl, undecyl, dodecyl, hexadecyl), Na, Li, K, a metal, or a halogen; R" is at least one of a —$CH_2$— group and a —$CH_2CH_2$— group; and n and x are each an 8-16 carbon chain that may be saturated or unsaturated, and that may or may not contain additional functional groups. In one embodiment, the lipid is asymmetrical.

Examples of lipid compositions of the presently disclosed and claimed inventive concept(s) include, but are not limited to, 2-carboxyheptadecanoyl heptadecylamide (CHHDA); 1,4-dipalmitoyl-tartarate-2,3-disuccinic acid (DPTSA); 1,4-dipalmitoyl-tartarate-2,3-diglutaric acid (DPTGA); 1,4-disteroyl-tartarate-2,3-disuccinic acid (DSTSA); and cholesteryl hemisuccinate (CHEMS).

The presently disclosed and claimed inventive concept(s) is also related to methods of producing said compositions comprising said lipids of the general formula [Awasthi, 2005]. The methods include the steps of reacting a saturated or unsaturated lipid dicarboxylic anhydride with another lipid containing at least one functional group, including but not limited to, an amine or hydroxyl functional group. The reaction is allowed to occur for appropriate duration of time in the presence or absence of solvents, such as but not limited to, pyridine or triethanolamine (tritheylamine). A general method of synthesizing such lipids is illustrated by the synthesis scheme discussed in Example 1. However, said synthesis scheme is to be understood to be provided for purposes of example only and is not to be construed as limiting.

The presently disclosed and claimed inventive concept(s) is further related to a liposome or other lipid nanostructure comprising the lipid compositions described herein above. Said liposome or other lipid nanostructure may further include other lipids, such as but not limited to, phospholipids. Specific examples of other lipids that may be utilized in accordance with the presently disclosed and claimed inventive concept(s) include, but are not limited to, at least one phosphatidylcholine, such as but not limited to, 1,2-disteroyl-sn-glycero-3-phosphatidylcholine (DSPC) and dipalmitoyl phosphatidylcholine (DPPC); at least one phosphoethanolamine, such as but not limited to, 1,2-disteroyl-sn-glycero-3-phosphatidylethanolamine (DSPE); at least one phosphatidylglycerol, such as but not limited to, dimyristoylphosphatidyl glycerol (DMPG); at least one sterol lipid, such as but not limited to, cholesterol; at least one vitamin, such as but not limited to, vitamin E; and the like. In one embodiment, the anionic non-phospholipid may comprise 1% to 30% of the total lipid present in the liposome/lipid nanostructure. In another embodiment, any phospholipid present in the liposome/lipid nanostructure will be in the range of from 30% to 99% of the total lipid present in the liposome/lipid nanostructure, so as to minimize any toxicity of the liposome/lipid nanostructure.

The liposome/lipid nanostructure may be provided with any particle size that will allow the liposome/lipid nanostructure to function in accordance with the presently disclosed and claimed inventive concept(s). In one embodiment, the liposome/lipid nanostructure may be provided with a particle size in a range of from about 50 nm to about 500 nm, such as but not limited to, about 200 nm to about 300 nm; in addition, the liposome/lipid nanostructure may be provided with a volume average particle size in a range of from about 10 nm to about 5,000 nm.

The lipids and liposome/lipid nanostructures formed therefrom in accordance with the presently disclosed and claimed inventive concept(s) have several advantages of the prior art, including but not limited to, a decrease in toxicity as well as a decrease in expense. Negative phospholipids are toxic to cells at certain concentrations; because of the absence of the phosphate group from the compositions of the presently disclosed and claimed inventive concept(s), the lipid (and thus the liposome/lipid nanostructures formed therefrom) do not induce untoward effects as commonly seen with liposomes containing anionic phospholipid. It is shown herein that the presence of the anionic non-phospholipid of the presently disclosed and claimed inventive concept(s) is not toxic to vascular endothelial cells nor to macrophages in culture, and that LEH preparations formed therefrom do not activate platelets in vitro. In addition, the lipid compositions of the presently disclosed and claimed inventive concept(s) are entirely synthetic and thus can be synthesized in large quantities using inexpensive raw materials and procedures. Further, the replacement of anionic phospholipids commonly used in liposome formulations with the anionic non-phospholipid compositions of the presently disclosed and claimed inventive concept(s) will increase encapsulation and stability of the liposomal structures.

The liposome/lipid nanostructure may further comprise at least one additional moiety. Moieties that may be utilized in accordance with the presently disclosed and claimed inventive concept(s) include, but are not limited to: (1) a targeting moiety such as but not limited to peptides that target the GRP receptor, including but not limited to, bombesin-related peptides; antibodies and antibody fragments; as well as small and large molecule ligands of known receptors and antigens; (2) a coating molecule attached to any phospholipids present in the liposome/lipid nanostructure to decrease the charge effect thereof, such as but not limited to, polyethylene glycol (PEG); (3) a labeling moiety, such as but not limited to, moieties that allow radiolabeling of the liposome structure, including but not limited to, diethylenetriamine pentaacetic acid; and the like.

In addition, the liposome/lipid nanostructure may have one or more molecules/agents encapsulated there within. Said molecules that may be incorporated within the liposome/lipid nanostructure include any molecules to be delivered to a patient. Examples include, but are not limited to, hemoglobin, therapeutic or diagnostic drugs and therapeutic peptides and proteins (such as but not limited to, interferon-gamma (IFN-γ); a reductant, such as but not limited to, glutathione, cystein, and homocysteine; an antioxidative enzyme, such as but not limited to, catalase and superoxide dismutase; an oxygen-affinity modifier, such as but not limited to, pyridoxal phosphate; other enzymes, such as but not limited to, glucose oxidase, glutathione peroxidase; chelating agents, such as but not limited to, deferoxamine; and combinations and derivatives thereof.

The molecule/agent encapsulated within the liposome/lipid nanostructure may also be a pharmaceutical agent, and encapsulation thereof will produce a pharmaceutical composition comprising the pharmaceutical agent encapsulated within the liposome/lipid nanostructure described in detail herein above. The pharmaceutical agent may be any molecule, protein and/or enzyme that provide a diagnostic or therapeutic effect to a patient to which the pharmaceutical composition is administered. Examples of pharmaceutical agents that may be utilized in accordance with the presently disclosed and claimed inventive concept(s) include, but are not limited to, antibiotic/antiviral/antifungal agents, such as but not limited to, amphotericin B and vancomycin; chemotherapeutic agents, such as but not limited to, doxorubicin; anti-inflammatory drugs, such as but not limited to, thalidomide; curcumin or a derivative thereof; diagnostic agents, such as but not limited to, iodinated X-ray and CT contrast agents; radiodiagnostic and radiotherapeutics, such as but not limited to, radionuclides Re-188, Tc-99m, 1-131 and other iodine isotopes, F-18, C-11, O-15, In-111; and the like.

The presently disclosed and claimed inventive concept(s) is yet further related to methods of producing the liposome/lipid nanostructure described herein above. Such methods include the steps of providing at least one anionic non-phospholipid composition as described herein above, disposing same in an aqueous solution, and dispersing the compositions to form the liposome/lipid nanostructure. The dispersion may be accomplished by any method that supplies a sufficient amount of energy to cause the lipid compositions to disperse into individual vesicles/liposomes/lipid nanostructures; said methods include, but are not limited to, sonication, extrusion, reverse phase evaporation, lyophilization, fluidized-bed, freeze thaw method, a method using a microfluidizer, and the like.

The presently disclosed and claimed inventive concept(s) further includes a method of forming a liposome/lipid nanostructure having at least one molecule/agent encapsulated therein, such as but not limited to, the pharmaceutical composition described herein above. Such method includes the steps of providing at least one anionic non-phospholipid composition as described herein above, providing the molecule/agent/pharmaceutical agent, disposing the anionic non-phospholipid composition and the molecule/agent/pharmaceutical agent in an aqueous solution, and dispersing same to form the liposome/lipid nanostructure having the molecule/agent/pharmaceutical agent encapsulated therein. The dispersion may be accomplished as described herein above. Alternatively, the anionic non-phospholipid composition may initially be dispersed to form a pro-liposome composition, and the pro-liposome composition mixed with the molecule/agent/pharmaceutical agent to encapsulate same and form the liposome/lipid nanostructure having the molecule/agent/pharmaceutical agent encapsulated therein.

The presently disclosed and claimed inventive concept(s) is also directed to a method of using the pharmaceutical composition described herein above. Said method includes the steps of providing the pharmaceutical composition comprising anionic non-phospholipid and pharmaceutical agent as described herein above, and administering an effective amount of the pharmaceutical composition to a patient in need thereof.

One non-limiting example of a pharmaceutical agent that may be utilized in accordance with the presently disclosed and claimed inventive concept(s) is the novel curcumin analog 3,5-bis(2-fluorobenzylidene)-4-piperidone (EF24). The compound was encapsulated inside the liposomes using the dehydration-rehydration method in the presence of EF24 solubilized in hydroxypropyl beta cyclodextrin (HPβCD). The use of cyclodextrin is not to be construed as limiting, as the cyclodextrin may be replaced with other solublizing substances, such as but not limited to, gamma cyclodextrin or various other derivatives of cyclodextrins. The EF24-liposomes are prepared for application in diseases such as but limited to cancer, inflammation and infection. A non-limiting example of a method of preparation of EF24-liposomes is described in detail in Example 2; however, said method is strictly for purposes of illustration only and is not to be construed as limiting.

The presently disclosed and claimed inventive concept(s) is further directed to a pharmaceutical composition/artificial oxygen carrier comprising liposome-encapsulated hemoglobin (LEH), wherein the liposome comprises the lipid of the general formula [1] and formed as described herein above. In one embodiment, the artificial oxygen carrier may further include at least one of a reductant, antioxidative enzyme and oxygen-affinity modifier (each of which is described in detail herein above) encapsulated therein, to enhance the resuscitative capacity of the liposome-encapsulated hemoglobin.

The hemoglobin utilized in accordance with the presently disclosed and claimed inventive concept(s) may be obtained from any source, including native hemoglobin derived from various living organisms as well as recombinant hemoglobin. In one embodiment, hemoglobin may be obtained from outdated red blood cell units. The hemoglobin may further be provided in a more stable form, such as but not limited to, carbonylhemoglobin. Alternatively, the presently disclosed and claimed inventive concept(s) also encompasses the use of any heme derivatives. The term "heme derivatives" as used herein will be understood to include any derivatives or compounds in which a porphyrin ring of heme is modified with a substituent and has a reversible oxygen-binding potential.

Hemoglobin may be present in the artificial oxygen carrier at any concentration sufficient to allow the LEH to function as an artificial oxygen carrier. In one embodiment, the concentration of hemoglobin present in the LEH is in a range of from about 5 g/dL to about 15 g/dL. In addition, in one embodiment, the particle size of the LEH is in a range of from about 200 nm to about 300 nm.

The presently disclosed and claimed inventive concept(s) is also directed to a method of forming said artificial oxygen carrier comprising liposome-encapsulated hemoglobin. Such method includes the steps of providing at least one anionic non-phospholipid composition as described herein above, providing an effective amount of hemoglobin, disposing the anionic non-phospholipid composition and the hemoglobin in an aqueous solution, and dispersing same to form the liposome having hemoglobin encapsulated therein. The dispersion may be accomplished as described herein above. When the artificial oxygen carrier comprises at least one of a reductant, antioxidative enzyme and oxygen-affinity modifier, said composition(s) may be provided and disposed in the aqueous solution prior to dispersal thereof to form the liposomal structures, or the composition(s) may be added to the liposomal structures after formation thereof. For example, the encapsulated material may be encapsulated during multilamellar liposome preparation wherein the dry lipid is exposed to the composition. Alternatively, the lipid may first be reduced into liposome form to provide proliposomes, followed by exposure of the proliposomes to the composition to be encapsulated therein.

The presently disclosed and claimed inventive concept(s) is further directed to a method of using the artificial oxygen carrier/liposome-encapsulated hemoglobin described herein above. Said method includes the step of providing the liposome-encapsulated hemoglobin and administering an effective amount of the LEH to a patient in need thereof. In one embodiment, the patient exhibits one or more of the following conditions: acute blood loss, surgery, anemia, hypovolemia, ischemia; in addition, LEH administration may be indicated to increase oxygen content in blood or tissue for enhanced chemotherapeutic or radiotherapeutic effect in diseases, such as but not limited to, cancer. LEH may also be used in situations where religious beliefs prohibit whole blood or RBC transfusion practice.

Examples are provided hereinbelow. However, the present inventive concept(s) is to be understood to not be limited in its application to the specific experimentation, results and laboratory procedures. Rather, the Examples are simply provided as one of various embodiments and is meant to be exemplary, not exhaustive.

EXAMPLE 1

This example provides a general synthesis scheme for one non-limiting example of anionic non-phospholipid constructed in accordance with the presently disclosed and claimed inventive concept(s).

Tetradecenylsuccinic anhydride (4.3 g, 17.8 mmole) and hexadecylamine (2.93 g, 10.4 mmol) were weighed in an oven-dried round bottom flask. Pyridine (4.5 ml) was added to the flask and the reaction was allowed to occur at 80° C. for 3 hr. The reaction mixture was extracted into dichloromethane (DCM, 150 ml) and washed with 10% HCl. The organic phase was separated, dried with sodium sulfate and concentrated to obtain white solid of unsaturated CHHDA (wt. 6.88 g, yield 96%). The unsaturated CHHDA was subjected to catalytic reduction to obtain saturated CHHDA. Briefly, unsaturated CHHDA was dissolved in hexane at 60° C. Reduction was carried out by passing hydrogen gas in presence of catalyst palladium/charcoal (5%, 40 mg) at atmospheric pressure for 16 hrs. The reaction mixture was filtered on a Buchner funnel and hexane was evaporated under vacuum to obtain CHHDA as white solid (wt. 5.36 g, yield 78%). $^1$H NMR (300 MHz, CDCl$_3$): δ 5.72 (br, 1H, NH, exchanged with D$_2$O), 3.25 (q, 2H, CH$_2$, J=3.6), 2.80-2.35 (m, 4H, CH$_2$), 1.60-1.40 (m, 4H, CH$_2$), 1.35-1.15 (m, 50H, CH$_2$), 0.87 (t, 6H, CH$_3$). $^{13}$C NMR (75 MHz, CDCl$_3$): δ 176.04, 171.43, 41.62, 37.41, 31.56, 31.51, 29.34, 29.30, 29.16, 29.00, 22.34, 13.85. ESI HRMS calculated for C$_{34}$H$_{68}$NO$_3$ (M$^+$+1) 538.42. found 538.40. CHHDA was also evaluated by differential scanning calorimetry (DSC) on a Q1000 (TA Instruments, New Castle, Del.).

EXAMPLE 2

Encapsulation of the novel curcumin analog 3,5-bis(2-fluorobenzylidene)-4-piperidone (EF24) in liposomes constructed in accordance with the presently disclosed and claimed inventive concept(s).

Formation of inclusion complexes: Inclusion complexes of EF24 with HPβCD were formed in the solution phase. EF24 (15 mg) was transferred to 2.5 ml of HPβCD solution (500 mg/ml). The mixture was continuously agitated on a shaker incubator at 25° C. for 72 hrs and then allowed to stand for 6 hrs. The mixture was centrifuged at 14000 rpm for 15 min and the supernatant collected was passed through 0.22 μm cellulose acetate sterile filter. The amount of HPβCD-solubilized EF24 was estimated spectrophotometrically at 315 nm. The HPβCD-EF24 inclusion complex was characterized by X-ray diffraction and differential scanning calorimetry.

Preparation of dehydration-rehydration vesicles (DRVs): The dehydration rehydration vesicles were prepared using a lipid composition described earlier. The phospholipid film was rehydrated with HYPURE™ endotoxin free cell culture grade water (Hyclone, Utah) to maintain total lipid concentration to 12 mM. The resulting suspension of multilamellar vesicles was either subjected to 8 FT cycles or sonication. An FT cycle included snap-freezing the suspension in liquid nitrogen, followed by immediate thawing in a 58° C. water bath. In case of sonication, a bath sonicator (Model 150D, VWR International, Pa.) was used, and liposomal suspension was sonicated for 45 min at 58° C. A 0.22 μm filtered solution of EF24-HPβCD inclusion complex in HYPURE™ water was added to the liposomal suspension in such a way that the DSPC:EF24 molar ratio remained either 1.43 or 4.73. The mixture was then vortexed for 30 sec and diluted with either 1% sucrose solution or phosphate buffered saline (PBS, pH 7.4) to provide a lipid concentration of 2 mM. The mixture was distributed in several sterile glass vials and lyophilized for 48 hrs in a Triad lyophilizer (Labconco, Mo.). The dried mass was rehydrated in a controlled manner, typical in dehydration rehydration procedures. The thick suspension formed was allowed to stand at 25° C. for 30 min and further diluted by several fold with Dulbecco's 10×PBS. The liposomes were purified from un-entrapped materials using a two step centrifugation process. The first step involved a low speed centrifugation (1500 rpm, 5 min). This step was repeated 3 times, each time transferring the supernatant into a sterile ultracentrifuge tube and washing the cake with 1×PBS. The low speed centrifugation removed free EF-24. The second step involved ultracentrifugation of the supernatant that was collected during the first step (35,000 rpm at 4° C. for 40 min). This step was also repeated three times as above. Free HPβCD, if any present, was removed during this step. The cake formed after final cycle was reconstituted to 400 μl volume with sterile PBS. Strict aseptic conditions were maintained during the entire experiment.

EXAMPLE 3

Materials and Methods for Example 3

Materials:

The chemicals were obtained from Sigma-Aldrich (St. Louis, Mo.) and/or various suppliers through VWR Scientific (West Chester, Pa.) and were used without further purification. Tetradecenyl succinic anhydride was a kind gift from Vertellus Specialties Inc (Indianapolis, Ind.). For liposome preparations, the phospholipids were purchased from Lipoid (Ludwigshafen, Germany), Avanti Polar Lipids (Alabaster, Ala.) or NOF Corporation, (Tokyo, Japan). Cholesterol was obtained from Calbiochem (Gibbstown, N.J.). Outdated red blood cell units were kind gift from Oklahoma Blood Institute (Oklahoma City, Okla.). For NMR and mass spectroscopy, analytical services in the Chemistry Department of the University of Oklahoma (Norman, Okla.) were used.

Synthesis of Anionic Nonphospholipids

Figure 1:
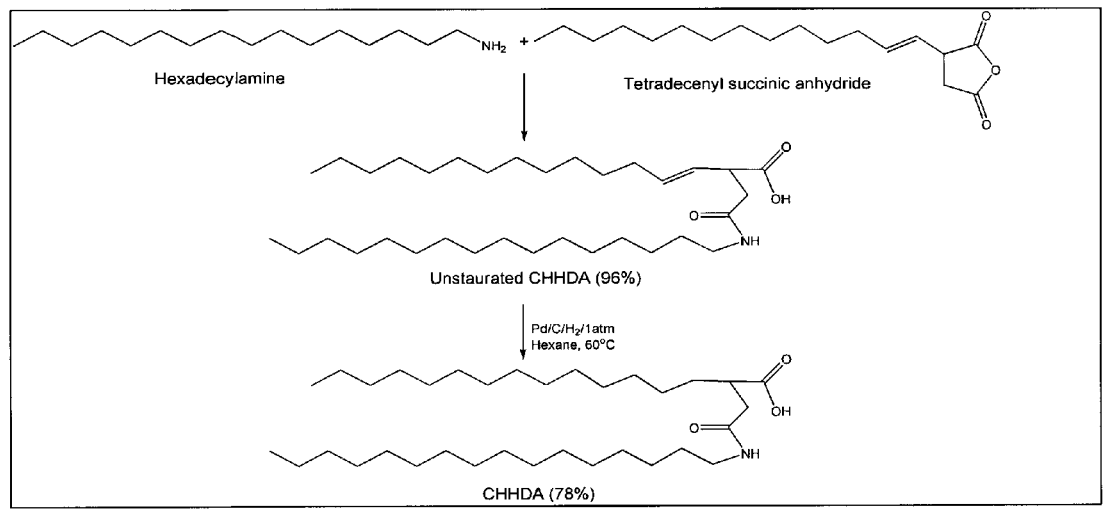
FIG. 1 illustrates a scheme for the synthesis of saturated CHHDA in accordance with the presently disclosed and claimed inventive concept(s).

2-Carboxyheptadecanoyl heptadecylamide
(CHHDA, FIG. 1)

The scheme for the synthesis of CHHDA is shown in FIG. 1. Tetradecenylsuccinic anhydride (4.3 g, 17.8 mmole) and hexadecylamine (2.93 g, 10.4 mmol) were weighed in an oven-dried round bottom flask. Pyridine (4.5 ml) was added to the flask and the reaction was allowed to occur at 80° C. for 3 hours. The reaction mixture was extracted into dichloromethane (DCM, 150 ml) and washed with 10% HCl. The organic phase was separated, dried with sodium sulfate and concentrated to obtain white solid of unsaturated CHHDA (wt. 6.88 g, yield 96%). The unsaturated CHHDA was subjected to catalytic reduction to obtain saturated CHHDA. Briefly, unsaturated CHHDA was dissolved in hexane at 60° C. Reduction was carried out by passing hydrogen gas in presence of catalyst palladium/charcoal (5%, 40 mg) at atmospheric pressure for 16 hours. The reaction mixture was filtered on a Buchner funnel and hexane was evaporated under vacuum to obtain CHHDA as white solid (wt. 5.36 g, yield 78%). $^1$H NMR (300 MHz, CDCl$_3$): δ 5.72 (br, 1H, NH, exchanged with D$_2$O), 3.25 (q, 2H, CH$_2$, J=3.6), 2.80-2.35 (m, 4H, CH$_2$), 1.60-1.40 (m, 4H, CH$_2$), 1.35-1.15 (m, 50H, CH$_2$), 0.87 (t, 6H, CH$_3$). $^{13}$C NMR (75 MHz, CDCl$_3$): δ 176.04, 171.43, 41.62, 37.41, 31.56, 31.51, 29.34, 29.30, 29.16, 29.00, 22.34, 13.85. ESI HRMS calculated for C$_{34}$H$_{68}$NO$_3$ (M$^+$+1) 538.42. found 538.40. CHHDA was also evaluated by differential scanning calorimetry (DSC) on a Q1000 (TA Instruments, New Castle, Del.). DSC was performed, courtesy Dr. Brian P. Grady, in the School of Chemical, Biological and Materials Engineering of the University of Oklahoma (Norman, Okla.).

Figure 2:
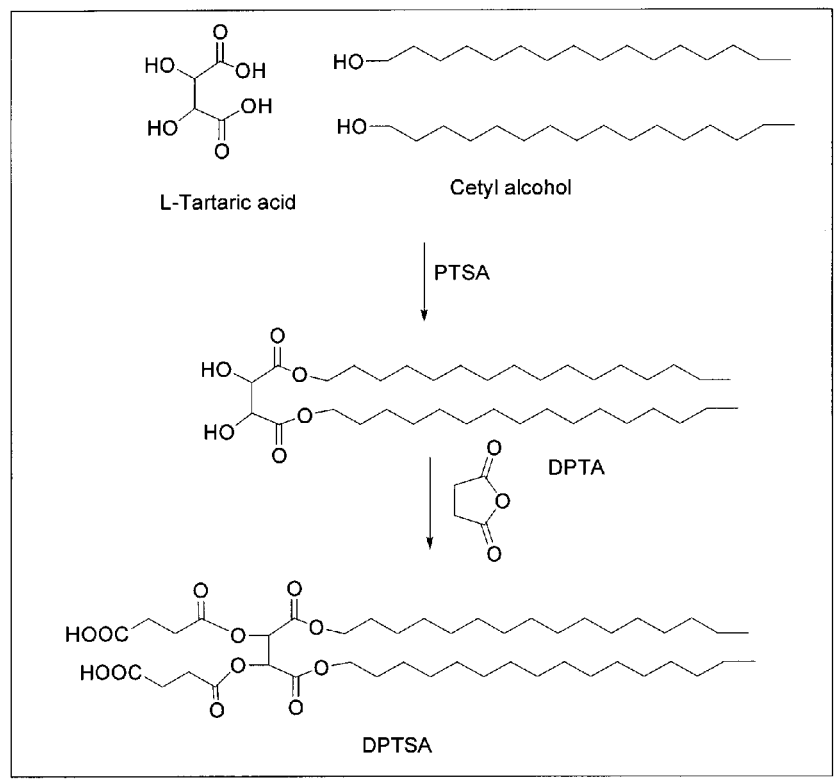
FIG. 2 illustrates a synthesis scheme for DPTSA in accordance with the presently disclosed and claimed inventive concept(s).

1,4-Dipalmitoyl-tartarate-2,3-disuccinic acid
(DPTSA, FIG. 2)

Cetyl alcohol (71 gm, 0.29 mol) and p-toluene sulfonic acid (PTSA, 30.4 gm, 0.16 mol) were added to a solution of tartaric acid (20 gm, 0.13 mol) in toluene. The reaction mixture was refluxed for 16 h using dean stark apparatus. The toluene layer was given a water wash (100 ml), and the organic phase was separated, dried over sodium sulfate and concentrated to obtain white solid of DPTA. The solid was recrystallized from DCM and hexane to get 1,4-dipalmitoyl tartarate (DPTA) as white crystalline solid (75 gm, 86% yield). The melting point was determined to be 40-41° C. $^1$H NMR (300 MHz, CDCl$_3$): δ 4.52 (s, 2H), 4.25 (t, 4H, CH$_2$), 1.75-1.60 (m, 4H, CH$_2$), 1.40-1.10 (m, 52H, CH$_2$), 0.87 (t, 6H, CH$_3$). Disuccinate ester of DPTA was synthesized by adding succinic anhydride (0.91 gm, 9.1 mmol) to a solution of DPTA (2 gm, 3.0 mmol) in pyridine (5 ml) and heating at 80° C. for 2 h. The resultant compound was extracted into chloroform (50 ml) and washed with 10% HCl followed by a water wash. The organic phase was dried over anhydrous sodium sulfate to obtain white solid of 1,4-dipalmitoyl-tartarate-2,3-disuccinic acid or DPTSA (2.45 gm, 94% yield, melting point 65° C.). $^1$H NMR (300 MHz, CDCl$_3$): δ 5.72 (s, 2H), 4.14 (t, 4H, CH$_2$, J=6.0), 2.80-2.65 (m, 4H, succinyl), 1.67-1.58 (m, 4H, CH$_2$), 1.32-1.20 (m, 52H, CH$_2$), 0.88 (t, 6H, CH$_3$, J=6.4). ESI HRMS calculated for C$_{44}$H$_{78}$NaO$_{12}$ (M$^+$+Na) 821.54. found 821.40.

Figure 3:
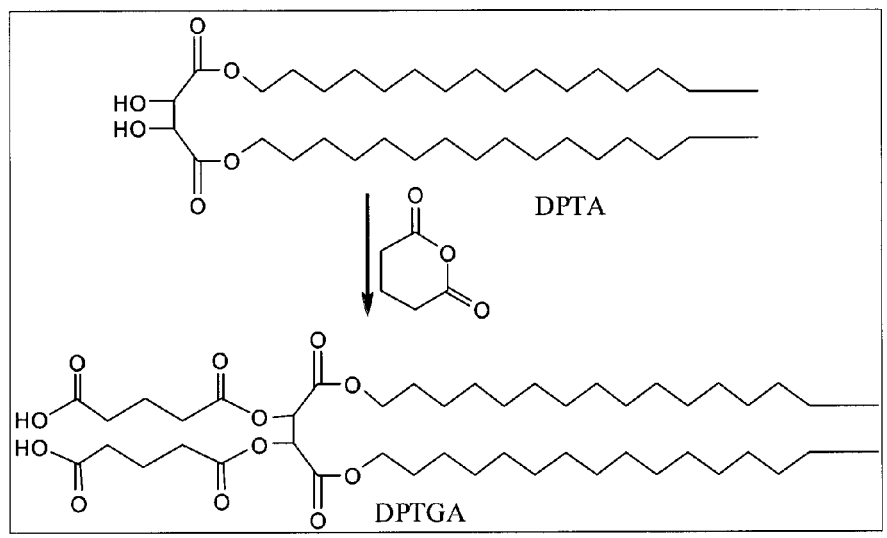
FIG. 3 illustrates a synthesis scheme for DPTGA in accordance with the presently disclosed and claimed inventive concept(s).

1,4-Dipalmitoyl-tartarate-2,3-diglutaric acid
(DPTGA, FIG. 3)

Glutaric anhydride (2.61 gm, 22.7 mmol) and 1,4-dipalmitoyl tartarate (6 gm, 9.17 mmol) in pyridine (15 ml) were heated at 80° C. for 2 h. The compound, 1,4-dipalmitoyl-tartarate-2,3-diglutaricacid (DPTGA) was extracted into chloroform (100 ml) and washed with 10% HCl (50 ml) followed by a wash with water (50 ml). The organic phase was separated, dried over Na$_2$SO$_4$ to obtain white solid (7.76 gm, 96% yield). $^1$H NMR (300 MHz, CDCl$_3$): δ 5.69 (s, 2H), 4.20-4.05 (m, 4H), 2.60-2.40 (m, 8H), 2.05-1.95 (m, 4H), 1.65-1.55 (m, 4H), 1.40-1.10 (m, 52H), 0.87 (t, 6H, CH$_3$).

1,4-Disteroyl-tartarate-2,3-disuccinic acid (DSTSA)

DSTSA was synthesized following the scheme similar to that used for DPTSA, except distearoyl tartaric acid ester (DSTA) was used as the starting lipid. DSTA was obtained commercially from VWR Scientific. DSTSA was collected as white solid (93% yield, melting point 81° C.). $^1$H NMR (300 MHz, CDCl$_3$): δ 5.75 (s, 2H), 4.20-4.05 (m, 4H, CH$_2$), 2.80-2.55 (m, 4H, succinyl), 1.70-1.55 (m, 4H, CH$_2$), 1.45-1.15 (m, 60H, CH$_2$), 0.88 (t, 6H, CH$_3$).

Figure 4:
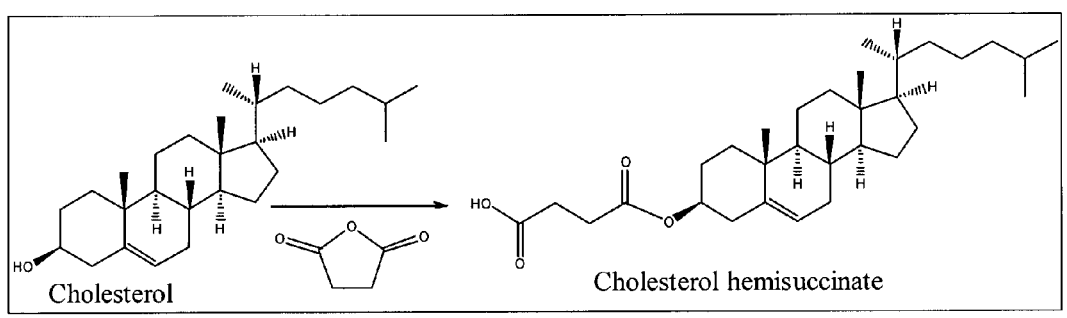
FIG. 4 illustrates a synthesis scheme for CHEMS in accordance with the presently disclosed and claimed inventive concept(s).

Cholesteryl Hemisuccinate (CHEMS, FIG. 4):

Succinic anhydride (1.55 gm, 15.5 mmol) was added to a solution of cholesterol (5 gm, 12.9 mmol) in pyridine (10 ml). After heating at 80° C. for 3 h, the reaction mixture was diluted with DCM and the organic phase was washed with 10% HCl (50 ml) followed by a water wash (50 ml). The organic phase was separated, dried over Na$_2$SO$_4$ to obtain cholesterol hemisuccinate as white solid. The solid was recrystallized from DCM and hexane (5.78 gm, 92% yield, and melting point 176-178° C.). $^1$H NMR (300 MHz, CDCl$_3$): δ 5.47 (d, vinylic-H, J=5.0), 4.70-4.60 (m, 1H), 2.75-2.65 (m, 4H), 2.38-2.35 (d, 7H), 2.20-1.80 (m, 12H), 1.60-1.40 (m, 12H), 0.78-0.75 (m, 3H).

Isolation of Stroma-Free Hemoglobin

Concentrated stroma-free hemoglobin was isolated from the outdated red blood cell (RBC) units using a previously described method [Sakai et al., 1993]. Outdated RBC units were obtained from Sylvan Goldman Center, Oklahoma Blood Institute (Oklahoma City, Okla.). To enhance the stability of hemoglobin during the isolation process, the RBC suspension was purged with 0.22 μm-filtered carbon monoxide gas (CO) which converts hemoglobin into a relatively more stable carbonylhemoglobin (CO-Hb). The carbonylated RBCs (20 g/dl, 300 ml) were mixed with dichloromethane (DCM, 60 ml) and mixed for 10 min. The precipitate was allowed to settle, and the supernatant was again extracted with DCM. The extraction was repeated 3 times to remove all the lipid material soluble in organic phase. The residual DCM in the aqueous phase containing CO-Hb solution was removed under vacuum in an R-210 rotavapor (Buchi Corporation, New Castle, Del.) at 40° C. in dark. The resultant CO-Hb solution was further heated at 60° C. for 1 hour to denature and precipitate any methemoglobin in the solution. The precipitate was removed by centrifugation at 8000 rpm for 20 min at 4° C. in a Sorvall RC-5B refrigerated superspeed centrifuge. The supernatant was purified from fine remnants of particulate matter by sequentially passing it through tangential-flow FiberFlow capsules having 100 and 50 nm cut-off (Minntech, Minneapolis, Minn.). Finally, the purified hemoglobin solution was concentrated to about 38 g/dl using a 30 kDa cut-off Prep/Scale-TFF filter cartridge (Millipore, Billerica, Mass.). The final preparation was characterized for oxygen affinity, CO-Hb content, MetHb concentration and endotoxin.

Preparation of Liposome-Encapsulated Hemoglobin (LEH)

The LEH was prepared in several steps described as follows:

Preparation of Pro-Liposomes:

Freeze-thaw (FT) method was used for the preparation of pro-liposomes. 1,2-disteroyl-sn-glycero-3-phosphatidylcholine (DSPC), cholesterol (CHO), anionic lipid, 1,2-disteroyl-sn-glycero-3-phosphoethanolamine-N-[monomethoxy poly (ethylene glycol) (5000)] (DSPE-PEG$_{5000}$) and vitamin E in 38.85:38.85:20:0.3:2 mol % were dissolved in a mixture of chloroform:methanol (2:1) and transferred to a round bottom flask. The solvent mixture was evaporated at 58° C. on rotavapor to form a thin film. Any trace of organic solvent was removed by keeping the film under vacuum for 12 h. The phospholipid film was rehydrated with sodium hydroxide solution equimolar to the carboxyl groups present in the anionic lipid to maintain total lipid concentration to 12 mM. The pH of the lipid suspension was adjusted to 6.8-7.0. This suspension of large multilamellar vesicles was subjected to 8 FT cycles. An FT cycle consisted of snap-freezing the suspension in liquid nitrogen followed by immediate thawing in a 58° C. water bath. DPPC-based pro-liposomes were prepared using DPPC, CHO, anionic lipid, DSPE-PEG$_{5000}$ and vitamin E in 38.85:38.85:20:0.3:2 mol % and processed as above except that the thawing was carried out at 42° C. After the final FT cycle, the pro-liposome suspension was shell-frozen in a lyophilization flask and subjected to a 48 h lyophilization cycle in a Triad Lyophilizer (Labconco, Kansas City, Mo.). The dried pro-liposome material was stored at −20° C. until further used.

Optimization of Hemoglobin Encapsulation:

The effect of synthesized anionic lipids on the efficacy of hemoglobin encapsulation was examined. The lyophilized DPPC-based pro-liposomes containing 20 mol % of the anionic lipid were allowed to warm up to 25° C., and the powder was aseptically and gradually added to a highly concentrated, purified 5 ml Hb solution (38 g/dl, <0.25 endotoxin units/ml) with constant stirring. The entire process was carried out under HEPA-filtered laminar flow hood; during entire processing, the temperature was maintained to 25° C. After 2 hours of incubation the suspension was ultracentrifuged at 35,000 rpm at 5° C. for 30 min in an Optima L-100 XP ultracentrifuge (Beckman Coulter, Fullerton, Calif.). The supernatant was removed and the pellet was resuspended in phosphate-buffered saline (PBS, pH 7.4). The centrifugation cycle was repeated two times to completely get rid of free hemoglobin. Finally the pellet was resuspended in 1.0 ml of PBS (pH 7.4) and the amount of encapsulated hemoglobin was determined by monitoring the absorbance of LEH lysate in OBG at 540 nm [Tomita et al., 1968]. In order to determine the effect of increasing mol % of anionic lipid on hemoglobin encapsulation, three batches of DPPC-based formulation were tested with 20, 28 and 40 mol % of CHHDA, and encapsulated Hb in respective formulations was estimated [Tomita et al., 1968].

Optimization of Homogenization Conditions:

The homogenization process was optimized separately using pro-liposome batches of identical composition, except that no hemoglobin was introduced in these preparations. The particle size of LEH was reduced by high pressure homogenization using Emulsiflex-C3 (Avestin Inc., Ottawa, Ontario, Canada). Parameters, such as number of homogenization cycles and pressure were optimized to obtain the LEH of size 200-300 nm.

Preparation of LEH:

In order to validate the optimized lipid composition and production protocol, two small LEH batches (LEH 1 and LEH 2, 25 ml each) were manufactured. The composition chosen was DPPC, CHO, CHHDA, DSPE-PEG$_{5000}$, vitamin E in 34.85:34.85:28:0.3:2 mol %. In batch LEH 2, the p50 of hemoglobin was adjusted by adding pyridoxal-5'-phosphate (PLP, 2.5 molar times of hemoglobin), to the carbonylhemoglobin solution and this solution was used for rehydration of lyophilized pro-liposomes. No PLP was used in LEH 1. Strict aseptic conditions were maintained throughout the preparation in a laminar flow hood. Final size reduction of hemoglobin containing pro-liposomes was carried out by high pressure homogenization in Emulsiflex-C3 at 20K psi for 4 cycles—each cycle separated by at least 30 minutes. The processing temperature was maintained at about 20° C. by immersing the heat transfer coil in an ice-cold water-bath. Further processing of LEH was performed according to the method earlier published [Awasthi et al., 2004; Awasthi et al., 2004A]. Briefly, the free hemoglobin was separated from encapsulated hemoglobin by tangential-flow filtration through 50 nm hollow fiber filter using PBS (pH 7.4) as the diluting solvent. The purified LEH was post-inserted with PEG-lipid by mixing an aqueous solution of DSPE-PEG$_{5000}$ with a dilute dispersion of LEH, such that the PEG-lipid concentration remains below its critical micelle concentration. To convert encapsulated carbonylhemoglobin into oxyhemoglobin, the PEGylated LEH was exposed to a bright visible light from a 500W halogen lamp under saturating oxygen atmosphere at 4-8° C. The conversion was monitored spectrophotometrically. The dilute oxygenated LEH was further subjected to tangential-flow filtration (50 nm filter, PBS wash-fluid) to eliminate remnants of free hemoglobin. Finally, the LEH was concentrated to the desired batch volume and stored at 4° C.

Characterization of LEH

To visually document the formation of liposomes using the anionic non-phospholipid, electron microscopy was performed at the University of Oklahoma at Norman (OK). The LEH preparations were characterized for hemoglobin content, methemoglobin, size, oxygen affinity, and lipid concentration. Hb encapsulation was estimated by monitoring the absorbance of the OBG lysate of LEH at 540 nm [Tomita et al., 1968]. The phospholipid concentration was determined by Stewart assay [Stewart, 1980]. Methemoglobin content was also measured [Matsuoka, 1997]. Oxygen affinity (p50) was measured in a Hemox-analyzer (TCS Scientific, New Hope, Pa.). Briefly, a 50 µl sample of LEH was dispersed in a 4 ml phosphate buffer (pH 7.4) containing albumin and an antifoaming agent. The mixture was incubated at 37° C. for 5 minutes and aspirated into the cuvette for dual wavelength spectrophotometry. The sample was purged with $N_2$ gas to $PO_2$<2.0 mm Hg, before allowing air to attain $PO_2$>140 mm Hg. The results were analyzed by HAS software provided with the instrument. The particle size was determined by photon correlation spectroscopy using a Brookhaven particle size analyzer equipped with Mass Option software. Zeta potential of preparations was measured in a Zeta PLUS Zeta potential analyzer (Brookhaven Instruments Corp, Holtsville, N.Y.). Zeta potential of LEH was estimated, both, before (non-PEGylated LEH) as well as after (PEGylated LEH) PEG post-insertion and the values were compared to zeta potential of empty liposomes containing 28% CHHDA or 20% DMPG. Preparations equivalent to about 40 µg of phospholipid in 1.5 ml of 0.22 µm filtered de-ionized water were scanned at 25° C. for 10 runs, each run consisting of 20 cycles. Zeta potential values were obtained as millivolt±standard error of mean.

Cell Culture and Cytotoxicity Studies

As a long-circulating oxygen carrier, LEH is expected to mostly interact with two cell types—endothelial cells in the vasculature and macrophages responsible for clearing particulate material. Human Umbilical Vein Endothelial Cells (HUVEC, ATCC, Manassas, Va.) were grown in M-199 medium supplemented with 10% (v/v) plain FBS, endothelial cell grown supplement (ECGS) (20 µg/ml), heparin (90 mg/L), penicillin G (100 U/ml) and streptomycin (100 µg/ml) (Sigma-Aldrich, St. Louis, Mo.). Cells were maintained at 37° C. in 5% $CO_2$ atmosphere. Cells were used after 3 passes for cytotoxicity study. RAW 264.7 cells (ATCC, Manassas, Va.) were grown in Dulbecco's modified Eagle's medium supplemented with 10% FBS (ATCC) at 37° C. in 5% $CO_2$ atmosphere. Cells were grown in 96-well plates at a density of $10^4$ cells/well. After 24 h of culture, the cells were treated with 100 µl of either, 1, 2 or 5 mg/ml of PEGylated or non-PEGylated LEH. Separately, cytotoxicity of empty liposomes carrying 10, 20 and 28 mol % of CHHDA was also evaluated (5 mg/ml, 100 µl). Empty liposomes containing 0 mol % CHHDA and those containing DMPG at 20 mol % were taken as controls for comparison. The cytotoxicity was measured as the decrease in hexosaminidase activity in cells after 24 h as described by Landegren [Landegren, 1984]. Para-nitrophenol-N-acetyl-beta-D-glucosaminide was used as the substrate for hexosaminidase enzyme.

Platelet Activation by LEH In Vitro

Fresh human whole blood (5 ml) was obtained from a normal healthy volunteer. The blood was anticoagulated by acid-citrate-dextrose solution (9 blood: 1 ACD, volume ratio). Platelet rich plasma (PRP) was separated from other cellular components by centrifugation at 150 g for 8 min. The aliquots of PRP (about 0.5 million platelets) were treated with 5 mg/ml of lipid as LEH. Two preparations of LEH were tested—one with PEG-coating and the other without PEG-coating. Adenosine diphosphate (ADP, 100 µM) was used as the positive control. After 5 and 30 min of incubation The samples were labeled with anti-human platelet antibodies for flow cytometry [Shigeta et al., 2003].

Murine antihuman monoclonal fluorescein isothiocyanate (FITC)-conjugated CD61 was used to identify all platelets. Murine antihuman monoclonal phycoerythrin (PE)-conjugated CD62P was used to detect platelet activation. Isotype controls were run in parallel with all monoclonal antibodies: FITC-conjugated immunoglobulin G1 and PE-conjugated immunoglobulin G1. All antibodies and isotype controls were obtained from eBioscience (San Diego, Calif.). Briefly, about 10 µl of 1:10 diluted PRP was incubated in the dark at room temperature with a mixture of 20 µl of FITC-conjugated CD61 antibody and 20 µl of PE-conjugated CD62 antibody (each equal to about 0.25 µg and 0.125 µg antibodies, respectively). After 20 minutes, the platelets were thrice washed with PBS, followed by overnight fixing with 1 mL of ice-cold 1% paraformaldehyde in dark at 4° C. The samples were subjected to flow cytometric analysis in the Core Facility at the OUHSC on a FACS Calibur (BD and Company, Franklin Lakes, N.J.) equipped with an argon ion laser and CellQuest software (BD and Company, Franklin Lakes, N.J.). Forward light scatter and 2 fluorescent signals were determined for each cell, and at least 10000 platelet events were collected. The platelet population was logic gated by a forward scatter versus side scatter dot plot gate and by an FITC-conjugated CD61 versus side scatter dot plot gate. CD62P-positive activated platelets were identified by fluorescein intensity greater than that of the appropriate isotype control staining sample. The frequencies of CD62P-positive platelets were expressed as percentages of the total platelet population [Shigeta et al., 2003].

Data Analysis:

Data are presented as mean±SD. The statistical differences were determined by the paired Student t test for $P<0.05$.

Results of Example 3

Several novel anionic non-phospholipids were synthesized to enable enhanced encapsulation of hemoglobin inside the liposomes. FIG. 1-4 show the synthetic scheme for various anionic non-phospholipids. The inventors' observations in the development of an optimized and improved LEH formulation based on these anionic non-phospholipids are recorded in following paragraphs.

The reaction yields for CHHDA were routinely above 75%. CHHDA was characterized by proton NMR and high resolution mass spectrometry (HRMS). The diagnostic spectroscopic data described below confirmed the successful synthesis of CHHDA. ESI-HRMS showed molecular ion peak at 538.40 and $^1$H NMR showed the disappearance of vinylic protons at δ 5.80-5.20 ppm. The lipid peak intensity at δ 1.35-1.15 ppm was increased indicative of the hexadecylamine esterification. In DSC, CHHDA lipid showed endothermic events around 50° C., prior to the melting at around 80° C. (FIG. 5). Noticeable exothermic events were observed around room temperature, and the lipid showed two melting events. The peak temperatures on the graph are printed by the instrument software. These may not be melting points, but are the temperatures corresponding to the maximum of the exothermic release of heat.

DPTGA formation was confirmed by the appearance of glutaric protons at δ 4.20-4.05, lipid $CH_2$ protons at 2.05-1.95 and 1.40-1.10 ppm as multiplets in $^1$H NMR. In case of DSTSA, the protons at the site of esterification shifted downfield to δ 5.69 from 4.52 ppm suggesting esterification. The stearoyl tartarate protons on —OH bearing carbons appeared as broad doublets at 4.50 ppm and shifted downfield to 5.75 as singlet after esterification of —OH groups. The succinyl protons appeared at 2.55-2.80 ppm as multiplets in $^1$H NMR spectrum. CHEMS showed melting point of 176-178° C. where as cholesterol has a melting point of 148-150° C. The succinyl protons of CHEMS appeared at δ 2.75-2.60 in $^1$H NMR.

The freeze-thaw method was used to prepare DSPC and DPPC based pro-liposomes, before encapsulation of hemoglobin. The particle size of DSPC-based pro-liposomes was reduced to 397.4±6 nm after 8 FT cycles (Table 1). When sonication was used along with thawing, the pro-liposomes were reduced to an undesirably small size (210-215 nm). In case of DPPC-based composition, pro-liposomes of size 441.0±18 nm were produced after only 4 FT cycles. The effect of bath-sonication during thawing was similar to that seen with DSPC pro-liposomes, and the final size of DPPC pro-liposomes was about 213±2 nm.

To investigate the effect of anionic lipids on hemoglobin encapsulation, DPPC based pro-liposome containing 20 mol % of one of the synthesized anionic lipids were incubated with carbonylhemoglobin solution. The hemoglobin content of CHHDA-containing liposomes was found to be the highest (3.15 g/dl) whereas the hemoglobin content of DPTGA containing liposomes was the lowest (1.55 g/dl) (Table 2). The hemoglobin-to-lipid ratio for CHHDA liposomes was 1.2. Methemoglobin formation in case of all the anionic lipids except CHEMS was less than 2%. For unknown and unexplored reasons, CHEMS tended to induce methemoglobin formation to the extent of 40% of total hemoglobin. The visible appearance of this preparation was dark brown whereas all other preparations were shiny deep red in color. Further, pro-liposomes containing increasing amounts of CHHDA were prepared to investigate the effect on Hb encapsulation. The Hb encapsulation was found to increase with increasing CHHDA mol % to a certain limit (FIG. 6). The highest encapsulation (4.02 g/dl) was observed with 28 mol % of CHHDA. At 40 mol %, CHHDA appeared to disrupt liposome structure as no LEH pellet was observed after ultracentrifugation. As maximum Hb encapsulation was with 28 mol % CHHDA, effect of 28 mol % CHHDA on the bilayer structure of liposomes was investigated by scanning electron microscopy. As shown in FIG. 7, electron micrographs of LEH showed typical structure of liposomes. In summary, CHHDA up to 28% can be used as an anionic lipid component in LEH preparations.

In a separate set of experiments, the homogenization process was optimized for pressure and number of passes. At 15K psi pressure, homogenization for 4 or 5 passes did not reduce the particle size below 400 nm (Table 3). Increasing the pressure to 20K psi produced the liposomes in 200 nm range. As the desired size range was achieved at a combination of 4 passes at 20K psi, this set of conditions was selected for scale up of manufacturing further batches of LEH. Two batches of LEH were prepared—one containing PLP and the other without PLP. LEH 1 and LEH 2 had particle size of 273.4±4.2 and 222.6±1.3 nm, respectively. LEH 1 and LEH 2 were characterized as described in Table 4. Both the batches had a high hemoglobin content and hemoglobin-to-lipid ratio. Both preparations had less than 2% methemoglobin. The entire LEH processing has been schematized in FIG. 8. Separately the possibility of CHHDA having any effect on the oxygen affinity of hemoglobin was investigated (Table 5). It is clear that even at 28 mole %, CHHDA does not have any significant impact on p50 value on its own. On the other hand, the addition of PLP to hemoglobin prior to encapsulation altered the p50 of the final product from about 19 to 33 Torr (Table 4). The p50 value of LEH 1 without PLP was 18.94, whereas LEH 2 with PLP had p50 value of 33.14 Torr.

TABLE 1

Sizes of Pro-liposomes after Freeze-thaw

| Phospholipid | FT cycle | Sonication? | Size (nm) |
|---|---|---|---|
| DSPC | 4 | — | 639.4 ± 13 |
| DSPC | 4 | Yes | 215.1 ± 2 |
| DSPC | 8 | — | 397.4 ± 6 |
| DSPC | 8 | Yes | 210.3 ± 3 |
| DPPC | 4 | — | 441 ± 18 |
| DPPC | 4 | Yes | 213.2 ± 2 |

TABLE 2

Effect of various anionic lipids on hemoglobin encapsulation

| Phospholipid | Mole % | Hb content (g/dL) | Hb/lipid |
|---|---|---|---|
| DPTA | 20 | 2.6 | 1.26 |
| DPTGA | 20 | 1.55 | 1.2 |
| DSTSA | 20 | 2.09 | 1.7 |
| CDHHA | 20 | 3.15 | 1.2 |
| CHEMS | 20 | Hb oxidation | — |

TABLE 3

Optimization of homogenization process

| Sr. No | Number of Passes | Pressure (psi) | Size (nm) |
|---|---|---|---|
| 1 | 4 | 15K | 405.1 ± 30 |
| 2 | 5 | 15K | 435.3 ± 16 |
| 3 | 5 | 20K | 199.1 ± 2.8 |
| 4 | 4 | 20K | 222.6 ± 1.3 |
| 5 | 3 | 22K | 263.7 ± 4 |

TABLE 4

Characteristics of LEH Batches

| Parameter | LEH 1 | LEH 2 |
|---|---|---|
| Size (nm) | 273.4 ± 4.2 | 222.6 ± 1.3 |
| Hb (g/dl) | 4.45 | 4.19 |
| Hb/Lipid ratio | 1.2 | 1.16 |
| p50 (Torr) | 18.94 | 33.14 |
| Met-Hb (%) | <2 | <2 |

TABLE 5

Effect of CDHHA on p50 of hemoglobin

| Sr. No. | TDSA-H (mol %) | p50 (Torr) |
|---|---|---|
| 1 | 0 | 9.94 |
| 2 | 20 | 10.18 |
| 3 | 28 | 10.85 |

Under the conditions of measurement, the zeta potentials of empty 20 mol % DMPG liposomes and empty 28% CHHDA liposomes were found to be −90.91±2.62 and −74.67±0.65 mV, respectively. Clearly, even at 28% concentration, the apparent negative potential of the CHHDA liposome particle was significantly lower than that of liposomes containing about $\frac{2}{3}^{rd}$ the amount of DMPG. The liposome's surface charge is governed by how the negatively-charged constituent is packed in the liposome structure, and how ionized the constituent becomes under measuring conditions. In comparison, the non-PEGylated LEH showed zeta potential value of −33.86±1.0. Presence of hemoglobin seemed to reduce negative potential of the liposome particles, possibly by interacting and neutralizing the negative charge of the liposome bilayer. PEGylation of LEH further reduced zeta potential to −27.98±2.4 mV. PEG coating of particles is known to decrease the charge effect under in vivo conditions.

As a long-circulating oxygen carrier, LEH is expected to mostly interact with two cell types—endothelial cells in the vasculature and macrophages responsible for clearing particulate material. The toxicity of the LEH formulation was investigated in HUVEC and RAW cell lines. Cells were grown in 96-well plates at a density of $10^4$ cells/well. After 24 h of culture, the cells were treated with LEH and empty liposomes carrying varying amounts of CHHDA or 20 mol % DMPG; the cytotoxicity was measured as the decrease in hexosaminidase activity in cells after 24 h. As shown in FIG. 9, the LEH showed no toxicity in the HUVEC or RAW cells as compared to controls (100%) at any concentration that was tested. Also no significant difference was observed in cytotoxicity pro of PEGylated and non-PEGylated liposome at the tested concentration (p>0.05). All the empty liposome formulations tested appeared to be non-toxic to the cells (p>0.05).

Previous studies have shown that liposome preparations, such as LEH have a tendency to activate platelets. A flow cytometry-based in vitro assay was performed to investigate if the LEH treatment activates platelets and whether PEGylation has any impact on this phenomenon. CD61 is a marker of platelet glycoprotein 111a, which is found on both normal (resting) and activated platelets. On the other hand, CD62P is found on the external membrane of activated platelets only. As shown in FIG. 10, LEH treatment did not demonstrate any platelet activation phenomenon. PEGylation of LEH had no effect on the LEH-mediated response of the platelets. Treatment with ADP (100 μm) caused about 56% activation of platelets. The results were identical when the lipid-platelet interaction was allowed to occur for 30 min (data not shown).

Discussion of Example 3

LEH is primarily mostly composed of a combination of saturated high-carbon phospholipids, such as distearoyl phosphatidylcholine (DSPC, $T_m$ 55° C.) and dipalmitoyl phosphatidylcholine (DPPC, $T_m$ 41° C.) and cholesterol. Although, hemoglobin encapsulation in the liposomes has not been possible to match hemoglobin content of RBCs, it is desirable to encapsulate large amounts of hemoglobin within a minimum amount of lipid. Hemoglobin interacts with the phospholipid bilayer by both hydrophobic and ionic forces [Szebeni et al., 1988]. Ionic interaction seems stronger than the hydrophobic interaction and is dependent on pH and ionic strength of the medium [Pitcher et al., 2002]. As such, negatively charged lipids enhance encapsulation by interacting with oppositely charged domains of proteins. Using about 9 mol % of DPPG, in conjunction with optimal encapsulating conditions, Tsuchida and coworkers achieved the Hemoglobin-to-lipid ratio of 1.61 [Sakai et al., 1996; Takeoka et al., 1996]. Below its isoelectric point, Hb carries a positive charge and electrostatically interacts with negatively charge lipids resulting in increased encapsulation [Sakai et al., 1996].

Apart from the beneficial interaction with hemoglobin, anionic lipids are known to undesirably enhance interaction of liposomes with complement and other opsonizing proteins in vivo [Miller et al., 1998; Szebeni, 1998; Semple et al., 1998]. Such interactions result in a rapid uptake of LEH by the RES, and toxic effects manifested as vasoconstriction, pulmonary hypertension, dyspnea, etc. Anionic phospholipids also enhance the rate of hemoglobin oxidation and displace heme relative to globin [Szebeni et al., 1988]. It is possible to partially reduce the toxicity of anionic phospholipids by PEG modification of LEH surface [Awasthi et al., 2004A]. It is believed that a hydrophilic PEG coating on the liposome surface creates a steric barrier, enabling liposomes to circulate longer [Torchilin et al., 1994]. Recently, the inventors have shown that PEGylation significantly reduces the thrombocytopenic effect of LEH administration in a rabbit model [Awasthi et al., 2007]. In view of the drawbacks of anionic phospholipids, an amino acid-based synthetic anionic lipid, 1,5-dipalmitoyl-1-glutamate-N-succinic acid, has been used in LEH [Sou et al., 2003]. It is believed that this amino acid-based lipid is better tolerated than anionic phospholipids.

The overall object of this work was to develop an LEH formulation with high Hb encapsulation based on ionic interaction with members of liposomal bilayer. In order to achieve this objective, several anionic lipids without phosphate groups were synthesized. Four structurally different anionic lipids, as well as a cholesterol hemisuccinate (CHEMS), were synthesized for this purpose. All the anionic lipids were synthesized keeping in mind that they will be incorporated as a component of liposome membrane. All the lipids have features normally observed in phospholipid and considered essential for stable liposome formation, except that they do not have a phosphate group. These include a polar head group, at least a 16-member carbon double chain and melting points and molecular weights in the range of commonly used phospholipid. Negative charge was imparted by having either one (CHHDA,) or two (DTPA, DSTSA, DPGA and CHEMS)—COOH groups on the polar head.

The first step in LEH production was to make either DSPC or DPPC based pro-liposomes containing the novel anionic lipids. FT method effectively produced pro-liposomes in the size range of 397-441 nm for DSPC and DPPC based pro-liposomes, respectively. FT cycles reduce the lamellarity of liposomes thus converting multilamellar vesicles into unilamellar vesicles. Reduction in lamellarity is helpful in increasing encapsulation efficiency on lipid basis. During freezing process ice crystals are formed and disrupt the bilayers. Disrupted bilayers reassemble to form newer vesicles. Thus FT increases population of vesicles while decreasing the lamellarity [Sou et al., 2003; Sriwongsitanont, 2004]. When FT process was coupled with sonication during thawing, the size reduction reached undesirably lower values. Hence the use of sonication was discontinued during further developmental stages. As expected, the number of cycles required to attain optimal pro-liposome size was dependent on the phospholipid used-DPPC (Tm=41° C.) pro-liposomes took fewer cycles than DSPC (Tm=55° C.) pro-liposomes. DPPC based formulation was considered more suitable for protein encapsulation due to milder processing conditions required. Hence this formulation was persisted with during further experiments.

The DPPC-based pro-liposomes were used to encapsulate hemoglobin. It was observed that liposomes containing CHHDA had the highest encapsulation efficiency. The experience with CHEMS was poor. Cholesterol is an essential component of most of the liposomes and is used sometimes as high as 50 mol %. An attempt was made to examine if some or all of the cholesterol can be replaced with CHEMS in LEH. It was believed that difference in the spatial orientation of CHEMS compared to anionic lipids in bilayers was responsible for the poor encapsulation. Somehow, CHEMS-containing LEH demonstrated high Met-Hb formation. The exact cause of superior performance of CHHDA is not known at this stage. CHHDA has only one —COOH group whereas other anionic lipids have two. This clearly indicates that the encapsulation is not a function of number of —COOH groups only. Orientation of lipids within the bilayer might affect packing of liposomes and rigidity. In this context it is worthwhile to note the inventors' observation that all preparations except those containing CHHDA revealed swelling-like phenomenon to varying degrees. Swelling did not increase with number of FT cycles and particle size was in the desired range of 400-450 nm immediately after FT. However pro-liposomes (except CHHDA) were observed to undergo gel formation after 24 hr which was an indication of vesicle fusion. This might have some relation to the low encapsulation efficiency observed with these lipids. Since CHHDA resulted in maximum Hb encapsulation, further optimization was carried out using this anionic lipid. As the highest Hb encapsulation (4.02 g/dl, Hb/lipid ratio 1.2) was observed at 28 mol % of CHHDA, LEH 1 and LEH 2 were prepared with 28 mol % of CHHDA. At 40 mol % of CHHDA, liposomes did not form. High mol % of CHHDA might have resulted in a very high electrostatic repulsion and disruption of bilayers.

The oxygen affinity is measured in terms of the partial pressure of oxygen required to saturate 50% of hemoglobin or p50. p50 of hemoglobin is altered by several allosteric modifiers. Since anionic lipids interact with hemoglobin fairly intimately, it was interesting to study if CHHDA at 28 mol % concentration influences p50 of Hb. There was insignificant effect of CHHDA on the p50 of encapsulated hemoglobin. More importantly, interaction between CHHDA and Hb did not affect the ability of PLP to enhance p50. PLP is an established allosteric modifier and its use in LEH2 easily altered p50 to 33 Torr. The inventors' previous experience suggested that LEH made up of the purified stroma-free hemoglobin (SFH) should have shown lower p50 value (<10 Torr). However, in case of LEH 1, the batch without PLP, the p50 value was about 19. The reasons for this discrepancy are not known, but are suggestive of some role played by the age of the outdated RBCs, state of their storage and the method of isolation. The previously reported purified SFH with high oxygen affinity was isolated from outdated RBCs kept frozen for several months; the isolation technique was based on hypotonic lysis of RBCs followed by sequential filtration through filters of decreasing pore size [Awasthi et al., 2004; Awasthi et al., 2004A]. In comparison, the SFH used in this work was from RBCs collected within 1 week of being outdated, kept at 4° C., and hemoglobin isolated by method based on the use of DCM [Sakai et al., 1993].

Using high-pressure homogenization, the inventors were able to reduce the particle size of LEH to a desired range. It has been reported earlier that the optimum size of PEGylated LEH for prolonged circulation after administration is 210-240 nm [Awasthi et al., 2004A].

As a long-circulating oxygen carrier, LEH is expected to mostly interact with two cell types—endothelial cells in the vasculature and macrophages responsible for clearing particulate material. The toxicity of the LEH formulation was studied in HUVEC and RAW cell lines. It was found that the presence of CHHDA in LEH is not toxic to the endothelial cells and macrophages in culture.

In addition, the LEH preparations containing CHHDA were not found to activate platelets in vitro. Studies in animal models receiving LEH or liposomes noted a formulation-dependent transient decrease in circulating platelets immediately following an intravenous infusion [Rabinovici et al., 1994]. Such an undesired reaction remains an obstacle to the successful application of LEH as a universal resuscitation fluid. The observation that in vitro platelet aggregation is not affected by incubation with LEH indicates an essential role of a systemic element in inducing platelet reaction [Phillips et al., 1997]. It has been since demonstrated that complement system plays an integral role in LEH-induced thrombocytopenia [Goins et al., 1997], causing activation of classical complement pathway after interaction between the phospholipid bilayer and C reactive protein. A recent article has also shown that anionic charge on the surface of the liposome plays a key role in activation of both classical and alternative complement pathway [Moghimi et al., 2006]. Liposomes containing negatively-charged phospholipids induce a very rapid decline in circulating platelets that is more severe, and that takes a longer time to recover to normal levels as compared to the liposomes consisting of neutral phospholipids. Liposomes containing phosphatidylglycerol form micro-aggregates with platelets in vitro, and it has been suggested that the sequestration of these micro-aggregates by the reticuloendothelial system causes the decline in circulating platelets [Loughrey et al., 1990].

The utility of LEH is most obvious when there is reduction in the oxygen carrying capacity secondary to a severe blood loss. Uncontrolled hemorrhage is also characterized by progressive depletion of circulating thrombocytes resulting in an inability to initiate effective hemostasis. In these circumstances, a further thrombocytopenic reaction to resuscitative fluid would exacerbate an already compromised hemostasis condition. Therefore, the LEH preparation should be formulated to eliminate the platelet reaction seen with liposome administration. The inventors recently reported the effect of charge and PEGylation on platelet activation by LEH in a rabbit model [Awasthi et al., 2007]. The tested LEH preparation contained dimyristoylphosphatidylglycerol (DMPG) as the anionic lipid.

Therefore, a formulation of LEH containing novel anionic non-phospholipid has been shown herein to enhance hemoglobin encapsulation. The LEH formulation was not toxic to endothelial cells and macrophages, and did not demonstrate any platelet activating tendency.

EXAMPLE 4

Effectiveness of LEH Resuscitation in a Rat Model of Hemorrhagic Shock

The effectiveness of LEH on cerebral energy metabolism was evaluated in a 40% hemorrhagic shock model in rats using proton and phosphorous magnetic resonance spectroscopy ($^1$H-MRS and $^{31}$P-MRS). The study lasted about 6 h, and animals infused with LEH survived the study duration. The study design is shown in FIG. 11. $^1$H-MRS data showed that the levels of markers of anaerobic metabolism, like lactate and pyruvate, increased post-bleeding but recovered closer to baseline levels after resuscitation with LEH. N-Acetylaspartate (NAA) also followed a similar trend. NAA is almost exclusively present in neurons, and its lower than normal levels indicate neuronal death. The fact that NAA levels return to the baseline after LEH resuscitation indicate the protective influence of LEH on neurons. The information obtained after $^{31}$P MRS also endorse the efficacy of LEH in oxygen delivery. The levels of PCr fall post-bleeding, which is an indication of ATP production at the expense of PCr via the creatine kinase pathway. Increase in Pi levels post bleeding suggest ATP breakdown. Both these markers return to their baseline levels after LEH resuscitation. The changes in ATP levels were monitored by following the γ-ATP peak, as γ-ATP and α-ATP peaks contain some contribution from β and α-ADP phosphates. The β-ATP level falls after bleeding (correlates well with post-bleed Pi increment) and recovers after LEH resuscitation. The trend followed by the metabolites described above is clearly indicative of a change of aerobic energy metabolism to an anaerobic pathway after bleeding and its return to aerobic pathway after LEH resuscitation. The observations that hemorrhage results in the appearance of a lactate peak in $^1$H-MRS and that the lactate peak disappears after LEH resuscitation demonstrate that LEH resuscitation is able to change post-bleeding anaerobic metabolism in the brain to an aerobic one. Also it can be concluded that $^1$H and $^{31}$P MRS are effective tools to study this alteration in the pattern of energy metabolism.

Thus, in accordance with the present inventive concept(s), there have been provided anionic lipid and liposome/lipid nanostructures, as well as methods of producing and using same, that fully satisfy the objectives and advantages set forth hereinabove. Although the inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the inventive concept(s).

REFERENCES

The following references, to the extent that they provide exemplary procedural or other details supplementary to those set forth herein, are specifically incorporated herein by reference.

V. D. Awasthi, D. Garcia, R. Klipper, W. T. Phillips, B. A. Goins, Int J Pharm, 283 (2004) 53-62

V. D. Awasthi, D. Garcia, R. Klipper, B. A. Goins, W. T. Phillips, J Pharmacol Exp Ther, 309 (2004) 241-248

V. D. Awasthi, Curr Drug Deliv, 2 (2005) 133-142

V. D. Awasthi, B. Goins, W. T. Phillips, Am J Pharmacol Toxicol, 2 (2007) 98-105

D. C. Drummond, O. Meyer, K. Hong, D. B. Kirpotin, D. Papahadjoulos, Pharmacol. Rev., 51 (1999) 691-743

M. C. Farmer, S. A. Johnson, R. L. Beissinger, J. L. Gossage, A. B. Lynn, K. A. Carter, Adv Exp Med Biol, 238 (1988) 161-170

B. Goins, W. T. Phillips, R. Klipper, A. S. Rudolph, The Journal of surgical research, 68 (1997) 99-105

U. Landegren, J Immunol Methods, 67 (1984) 379-388

H. C. Loughrey, M. B. Bally, L. W. Reinish, P. R. Cullis, Thrombosis and haemostasis, 64 (1990) 172-176

T. Matsuoka, Biol Pharm Bull, 20 (1997) 1208-1211

C. R. Miller, B. Bondurant, S. D. McLean, K. A. McGovern, D. F. O'Brien, Biochemistry, 37 (1998) 12875-12883

S. M. Moghimi, I. Hamad, T. L. Andresen, K. Jorgensen, J. Szebeni, Faseb J, 20 (2006) 2591-2593

W. T. Phillips, R. Klipper, D. Fresne, A. S. Rudolph, M. Javors, B. Goins, Exp Hematol, 25 (1997) 1347-1356

W. T. Phillips, R. W. Klipper, V. D. Awasthi, A. S. Rudolph, R. Cliff, V. Kwasiborski, B. A. Goins, J Pharmacol Exp Ther, 288 (1999) 665-670

W. H. Pitcher, 3rd, S. L. Keller, W. H. Huestis, Biochim Biophys Acta, 1564 (2002) 107-113

R. Rabinovici, A. S. Rudolph, J. Vernick, G. Feuerstein, Critical care medicine, 22 (1994) 480-485

A. S. Rudolph (Eds), Encapsulation of hemoglobin in liposomes, Birkhauser, Boston, 1995.

H. Sakai, S. Takeoka, H. Yokohama, Y. Seino, H. Nishide, E. Tsuchida, Protein Expr Purif, 4 (1993) 563-569

H. Sakai, K. Hamada, S. Takeoka, H. Nishide, E. Tsuchida, Biotechnol Prog, 12 (1996) 119-125

S. C. Semple, A. Chonn, P. R. Cullis, Adv. Drug Delivery Rev., 32 (1998) 3-17

K. Shigeta, N. Taniguchi, K. Omoto, S. Madoiwa, Y. Sakata, M. Mori, K. Hatake, K. Itoh, J Ultrasound Med, 22 (2003) 365-373

K. Sou, Y. Naito, T. Endo, S. Takeoka, E. Tsuchida, Biotechnol Prog, 19 (2003) 1547-1552

M. U. S. Sriwongsitanont, Colloid Polym Sci, 282 (2004) 753-760

J. C. M. Stewart, Anal. Biochem., 104 (1980) 10-14

J. Szebeni, H. Hauser, C. D. Eskelson, R. R. Watson, K. H. Winterhalter, Biochemistry, 27 (1988) 6425-6434

J. Szebeni, H. Hauser, C. D. Eskelson, K. H. Winterhalter, Biomater Artif Cells Artif Organs, 16 (1988) 301-312

J. Szebeni, Crit. Rev Ther Drug Carrier Syst, 15 (1998) 57-88

J. Szebeni, L. Baranyi, S. Savay, M. Bodo, D. S. Morse, M. Basta, G. L. Stahl, R. Bunger, C. R. Alving, Am J Physiol Heart Circ Physiol, 279 (2000) H1319-1328

M. Takaori, A. Fukui, Artif Cells Blood Substit Immobil Biotechnol, 24 (1996) 643-653

S. Takeoka, T. Ohgushi, K. Terase, T. Ohmori, E. Tsuchida, Langmuir, 12 (1996) 1755-1759

E. Y. Tomita S, Santa M, Yoshida H, Yasumitsu Y., J Nara Med Assoc, 19 (1968) 1-6

V. P. Torchilin, M. I. Papisov, J. Liposome Res., 4 (1994) 725-739

A. Usuba, R. Motoki, K. Sakaguchi, K. Suzuki, T. Kamitani, Artif Cells Blood Substit Immobil Biotechnol, 22 (1994) 503-516

P. Walde, S. Ichikawa, Biomol. Eng., 18 (2001) 143-177

What is claimed is:

1. A composition, comprising:
an anionic non-phospholipid having the structure represented by the following general formula [1]:

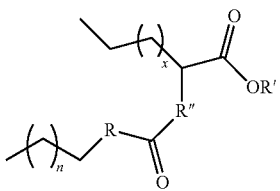

wherein R is NH; R' is at least one of H, an alkyl group, Na, Li, K, a metal, and a halogen; R" is at least one of a —CH$_2$— group and a —CH$_2$CH$_2$— group; and n is an 8-16 carbon chain and x is an 8-16 carbon chain.

2. The composition of claim 1, wherein the anionic non-phospholipid is 2-carboxyheptadecanoyl heptadecylamide (CHHDA).

3. A liposomal structure comprising:
an anionic non-phospholipid having the structure represented by the following general formula [1]:

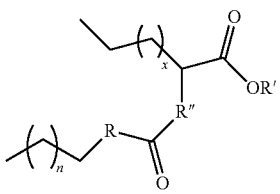

wherein R is NH; R' is at least one of H, an alkyl group, Na, Li, K, a metal, and a halogen; R" is at least one of a —CH$_2$— group and a —CH$_2$CH$_2$— group; and n is an 8-16 carbon chain and x is an 8-16 carbon chain.

4. The liposomal structure of claim 3, wherein the anionic non-phospholipid is present in a range of from about 1% to about 30% of the total lipid present in the liposomal structure, and wherein the liposomal structure comprises a particle size in a range of from about 50 nm to about 500 nm, and a volume average particle size in a range of from about 10 nm to about 5,000 nm.

5. The liposomal structure of claim 3, wherein the anionic non-phospholipid is 2-carboxyheptadecanoyl heptadecylamide (CHHDA).

6. The liposomal structure of claim 3, further comprising at least one phospholipid selected from the group consisting of phosphatidylcholine, phosphoethanolamine, and phosphatidylglycerol, and wherein the at least one phospholipid is present in a range of from about 30% to about 99% of the total lipid present in the liposomal structure.

7. The liposomal structure of claim 3, further comprising at least one molecule encapsulated therein, wherein the at least one molecule encapsulated therein is selected from the group consisting of a therapeutic molecule, a reductant, an antioxidative enzyme, an oxygen-affinity modifier, an enzyme, a chelating agent, a pharmaceutical agent, antibiotic agents, antiviral agents, antifungal agents, chemotherapeutic agents, anti-inflammatory drugs, curcumin or a derivative thereof, diagnostic agents, radiodiagnostic and radiotherapeutic agents, and combinations thereof.

8. The liposomal structure of claim 7, wherein the at least one molecule encapsulated therein is at least one of hemoglobin and 3,5-bis(2-fluorobenzylidene)-4-piperidone (EF24).

* * * * *

UNITED STATES PATENT AND TRADEMARK OFFICE
CERTIFICATE OF CORRECTION

PATENT NO. : 9,173,839 B2
APPLICATION NO. : 13/863000
DATED : November 3, 2015
INVENTOR(S) : Awasthi et al.

It is certified that error appears in the above-identified patent and that said Letters Patent is hereby corrected as shown below:

In the Specification:
Column 7, line 33: Delete "1-131" and replace with -- I-131 --
Column 18, line 61: Delete "111a," and replace with -- IIIa, --

Signed and Sealed this
Eighth Day of March, 2016

Michelle K. Lee
*Director of the United States Patent and Trademark Office*